(12) United States Patent
De Koning et al.

(10) Patent No.: US 7,906,491 B2
(45) Date of Patent: Mar. 15, 2011

(54) COMPOUNDS FOR MODULATING THE ACTIVITY OF EXCHANGE PROTEINS DIRECTLY ACTIVATED BY CAMP (EPACS)

(75) Inventors: John De Koning, The Hague (NL); Anne Christensen, Bergen (NO); Frank Schwede, Bassum (DE); Hans Gottfired Genieser, Lemwerder (DE); Stein Doskeland, Nesttun (NO); Johannes Bos, Bunnik (NL)

(73) Assignee: Univisitair Medisch Centrum Utrecht, Utrecht (NL)

( * ) Notice: Subject to any disclaimer, the term of this patent is extended or adjusted under 35 U.S.C. 154(b) by 1385 days.

(21) Appl. No.: 10/517,564

(22) PCT Filed: Jun. 10, 2003

(86) PCT No.: PCT/EP03/06120
§ 371 (c)(1),
(2), (4) Date: Dec. 15, 2005

(87) PCT Pub. No.: WO03/104250
PCT Pub. Date: Dec. 18, 2003

(65) Prior Publication Data
US 2006/0100166 A1 May 11, 2006

(30) Foreign Application Priority Data
Jun. 7, 2002 (EP) .................................... 02077219

(51) Int. Cl.
*A61K 31/70* (2006.01)
*C07H 19/213* (2006.01)

(52) U.S. Cl. ....................................... 514/47; 536/26.13

(58) Field of Classification Search .................. None
See application file for complete search history.

(56) References Cited

U.S. PATENT DOCUMENTS 3,712,885 A * 1/1973 Weimann et al. ........... 536/26.12
5,559,102 A * 9/1996 Yano et al. ...................... 514/46

FOREIGN PATENT DOCUMENTS

| JP | 2233692 A | 9/1990 |
| JP | 2258797 A | 10/1990 |
| JP | 3072493 A | 3/1991 |
| JP | 9295915 A | 11/1997 |
| JP | 11-130792 A | * 5/1999 |
| JP | 11130792 A | 5/1999 |
| JP | 3773148 B2 | * 5/2006 |

OTHER PUBLICATIONS

Schwede et al., "8-Substituted cAMP Analogues Reveal Marked Differences in Adaptability, Hydrogen Bonding, and Charge Accommodation between Homologous Binding Sites (AI/AII and BI/BII) in cAMP Kinase I and II," Biochemistry, 39(30), 8803-8812 (Jul. 7, 2000).*

Enserink et al., "A Novel Epac-specific cAMP Analogue Demonstrates Independent Regulation of Rap1 and ERK," Nature Cell Biology, 4(11), 901-906 (Oct. 28, 2002).*

Peters et al., "Selective Induction of Gene Expression and Second-messenger Accumulation in Dictyostelium discoideum by the Partial Chemotactic Antagonist 8-p-chlorophenylthioadenosine 3',5'-cyclic Monophosphate," Proc. nat. Acad, Sci USA, 88, 9219-9223 (Oct. 1991).*

Sopchik et al., "Conformations of the Phosphorus-containing Rings of Nucleoside Cyclic 3',5'-Phosphoramidates. The Questions of the Chair or Twist Free Energy Change for cAMP," Journal of Organic Chemistry, 56(20), 5911-5918 (Sep. 1991).*

Kataoka et al., "Studies on the Synthesis of Compounds Related to Adenosine-3',5'-Cyclic Phosphate. VI. Synthesis and Cardiac Effects of N6, N6,2'-O-trialkyl-, N6, 2'-O-dialkyl-, and 2'-O-Alkyladenosine-3',5'-Cyclic Phosphate," Chem. & Pharmaceutical Bull. (Japan), 38(6), 1596-1600 (1990).*

Ikehara, M., "2'-Substituted 2'-Deoxypurinenucleotides, Their Conformation, and Properties," Heterocycles, 21(1), 75-90 (1984).*

Gulyaev et al., "Synthesis of 2'-substituted Derivatives of 8-Hydroxyadenosine 3',5'-Cyclic Phosphate," Bioorganischeskaya Khimiya, 7(4), 552-558 (1981); only Abstract provided.*

Broeders et al. "A $^{31}$P NMR Stereochemical and Kinetic Study of the Alkaline Hydrolysis of *cis*-Nucleoside 3',5'-Cyclic Aryl [$^{18}$O]Monophosphates and Unlabled Analogs", Amer Chem Society (1992), vol. 114, No. 24, pp. 9624-9633.

Ichiba et al. "Characterization of GFR, a novel guanine nucleotide exchange factor for Rap1" FEBS Letters (1999) vol. 457:85-89.

McPhee et al. "Use of an activiation-specific probe to show that Rap1A and Rap1B display different sensitivities to activation for forskolin in Rat1 cells" FEBS Letters (2000) vol. 477: 213-218.

Rooij et al. "Epac is a Rap 1 quanine-nucleotide-exchange factor directly activated by cyclic AMP" Nature (1998) vol. 396: 474-477.

Uesugi, S. et al., "Carbon-13 NMR spectrum of 2'-fluoro-2'-deoxyadenosine 3',5'-cyclic phosphate" Heterycycles, (1982) vol. 17, issue 1, pp. 285-288 (previously cited as: C6: Caesar accession No. 1796, AN: 96:143250 CA).

* cited by examiner

Primary Examiner — Lawrence E Crane
(74) Attorney, Agent, or Firm — Morgan, Lewis & Bockius LLP; Richard F. Trecartin

(57) ABSTRACT

The present invention relates to novel compounds for modulating the activity of exchange proteins directly activated by cAMP (Epacs). In particular, the present invention relates to cAMP analogues that specifically modulate the activity of Epacs. Examples of the compounds of the invention are substituted deoxyadenosine-cyclic monosphosphates.

The invention further relates to pharmaceutical compositions comprising the novel compounds, and the use of the compounds in the treatment of diseases like cancer, chronic inflammation, thrombosis and/or type-2 diabetes mellitus in humans and/or animals.

36 Claims, 9 Drawing Sheets

```
Epac1       F G Q L A L Y N D A - - - - - - - - P R A A T I I
Epac2-B     F G K L A L V N D A - - - - - - - - P R A A S I V
PKARIa-A    F G E L A L I Y G T - - - - - - - - P R A A T V K
Olfactory   F G E I S I L N I K G S K M G N - R R T A N I R
Pacemaker   F G E M V H L Y A K P G K S N A D V R A L T Y C
CAP         I G E L G L F E E G Q E R S - A W V R A K T A C
```

COMPOUNDS FOR MODULATING THE ACTIVITY OF EXCHANGE PROTEINS DIRECTLY ACTIVATED BY CAMP (EPACS)

This application is a U.S. National Phase Filing under 35 U.S.C. 371 of International Application No. PCT/EP03/06120, filed on Jun. 10, 2003, which claims the benefit under 35 U.S.C. 365(c) of European Application No. 02077219.0, filed on Jun. 7, 2002.

The present invention relates to novel compounds for modulating the activity of exchange proteins directly activated by cAMP (Epacs). In particular, the present invention relates to cAMP analogues that specifically modulate the activity of Epacs. The invention further relates to pharmaceutical compositions comprising the novel compounds, and the use of the compounds in the treatment of humans and/or animals.

Epacs are a family of guanine nucleotide exchange factors for small GTPases of the Ras family. These proteins are activated by direct binding of cAMP. cAMP, the first identified and well studied second messenger (1), plays a role in a wide variety of cellular processes.

Generally it was assumed that the effects of cAMP are mediated by protein kinase A (PKA), the ubiquitously expressed intracellular receptor for cAMP, although additional cAMP targets have been described, like the olfactory and pacemaker channels.

Recently, however, a family of Rap1 guanine nucleotide exchange factors directly activated by cAMP [Epac1 and Epac2 (also known as cAMP-GEFI and cAMP-GEFII)] (2-4) was identified. These widely-expressed proteins contain a cAMP binding pocket that is very similar to the cAMP binding pocket in the regulatory subunits of PKA, and cAMP is critically required for exchange activity of Epac1 and Epac2 towards the small GTPases Rap1 and Rap2.

Commonly used reagents to activate PKA, like forskolin, which activates adenylate cyclase, and 8-Br-cAMP, activate both the PKA- and the Epac-mediated signalling pathways. The object of the present invention is to provide novel compounds which specifically modulate the Epac-Rap1 signalling pathway.

This object is achieved by providing a novel compound having the structural formula (I):

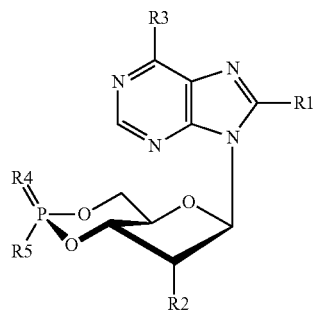

and deaza-analogues thereof, wherein:

$R_1$ can be independently H, halogen, azido, alkyl, aryl, amido-alkyl, amido-aryl, OH, O-alkyl, O-aryl, SH, S-alkyl, S-aryl, SeH, Se-alkyl, Se-aryl, amino, NH-alkyl, NH-aryl, N-bisalkyl, N-bisaryl, cycloalkylamino;

$R_2$ can be independently H, halogen, azido, O-alkyl, S-alkyl, Se-alkyl, NH-alkyl, N-bisalkyl, alkyl-carbamoyl, cycloalkylamino, silyl;

$R_3$ can be independently H, halogen, OH, azido, amido-alkyl, amido-aryl, O-alkyl, O-aryl, SH, S-alkyl, S-aryl, amino, NH-alkyl, NH-aryl, N-bisalkyl, N-bisaryl, NH-alkyl-carbamoyl, cycloalkylamino;

and wherein $R_4$ is O(H) or S(H); and $R_5$ is O(H), S(H), amino, H, alkyl, O-alkyl, O-aryl, S-alkyl, S-aryl, NH-alkyl, NH-aryl, N-bisalkyl, N-bisaryl; or $R_4$ is O(H), S(H), amino, H, alkyl, O-alkyl, O-aryl, S-alkyl, S-aryl, NH-alkyl, NH-aryl, N-bisalkyl, N-bisaryl; and $R_5$ is O(H) or S(H);

and pharmaceutically acceptable salts, esters, and/or solvates thereof, with the exception of 2'-deoxyadenosine-3',5'-cyclic monophosphate; $N^6$-monobutyryl-2'-deoxyadenosine-3',5,-cyclic monophosphate; 2'-deoxyadenosine-3',5'-cyclic monophosphorothioate;, 2'-deoxyadenosine-3',5'-cyclic monophosphoroanilidate; 2'-deoxyadenosine-3',5'-cyclic monophosphate methyl triester; 2'-deoxyadenosine-3',5'-cyclic monophosphate ethyl triester; 2'-O-methyladenosine-3',5'-cyclic monophosphate; ; 2'-O-ethyladenosine-3',5'-cyclic monophosphate; 2'-O-n-propyladenosine-3',5'-cyclic monophosphate; 2'-O-n-butyladenosine-3',5'-cyclic monophosphate; 2'-O-iso-butyladenosine-3',5'-cyclic monophosphate; 2'-O-methyladenosine-3',5'-cyclic monophosphate methyl triester; 2'-O-methyladenosine-3',5'-cyclic monophosphate phenyl triester.

In the research that led to the present invention it was found that Epacs differ from PKA in the cAMP binding domain on at least one critical amino acid. In addition, it has been found that by eliminating the hydroxy (—OH) of the 2'-position, the compound thus obtained is able to discriminate between Epac and protein kinase A.

According to the present invention novel compounds, in particular CAMP analogues with a modified 2'-O-ribose group, were thus identified and synthesized, such as 8-(4-chlorophenylthio)-2'-O-methyladenosine-3',5'-cyclic monophosphate(8-pCPT-2'-O-Me-cAMP) which specifically bind and modulate Epacs, but not PKA, in vitro.

It was found that by using these analogues, such as 8-pCPT-2'-O-Me-cAMP, in vivo, Rap1 is activated efficiently, whereas PKA-mediated responses are not induced. 8-pCPT-2'-O-Me-cAMP affected neither the activation nor the inactivation of extracellular signal-regulated kinase (ERK). Instead, it was found that cAMP-induced ERK activation was critically dependent on PKA and Ras, whereas Rap1 activity was completely dispensable. These results clearly demonstrate that cAMP-induced Rap1 activation and cAMP regulation of ERK are independent processes.

In a preferred embodiment of the invention $R_1$ is H, halogen, azido, O-alkyl, O-aryl, S-alkyl, S-aryl, NH-alkyl, NH-aryl, Se-aryl, more preferably $R_1$ is H, halogen, azido, O-alkyl, O-aryl, S-alkyl, S-aryl, NH-alkyl, NH-aryl, Se-aryl.

In a further preferred embodiment of the invention $R_1$ is H, Br, Cl, I, azido, 2-chlorophenylthio, 3-chlorophenylthio, 4-chlorophenylthio, 2-bromophenylthio, 3-bromophenylthio, 4-bromophenylthio, methylamino, methylthio, ethylthio, n-propylthio, n-butylthio, n-pentylthio, n-hexylthio, 2-fluorophenylthio, 3-fluorophenylthio, 4-fluorophenylthio, 4-methylcumarinyl, naphtyl-2-thio, phenylthio, 4-nitrophenylthio, 2-aminophenylthio, 3-aminophenylthio, 4-aminophenylthio, benzylthio, phenylethylamino, 3-phenyl-propylamino, 2-methoxyphenylthio, 3-methoxyphenylthio, 4-methoxyphenylthio, isopropylthio, benzimidazolyl-2-thio, 2-hydroxyethylthio, 2-aminoethylthio, pyridinylthio, benzothiazolylthio, 2-methylphenylthio, 3-methylphenylthio, 4-methylphenylthio, 2-isopropylphenylthio, 4-isopropylphenylthio, 2,3,5,6-tetrafluorophenylthio, 4-hydroxyphenylthio, 2,4-dichlorophenylthio, methoxy, ethoxy, propioxy, butoxy, benzyloxy, 4-methylbenzyloxy, 4-methoxybenzyloxy, 4-fluorobenzyloxy, 4-chlorobenzyloxy, 4-bromobenzyloxy, phenyloxy, cyclohexylamino, benzylamino, phenylseleno, 4-isopropyloxyphenylthio, 4-methylthiophenylthio, 6-aminohexylamino, 2,3-dichlorophenylthio, 2,5-dichlorophenylthio, 2,4-difluorophenylthio, 2,5-dimethoxyphenylthio, 2,5-dimethylthiophenylthio, 2,6-dimethylthiophenylthio, 2,6-dichlorophenylthio.

Preferably, $R_1$ is H, Br, Cl, azido, 2-chlorophenylthio, 3-chlorophenylthio, 4-chlorophenylthio, 2-bromophenylthio, 3-bromophenylthio, 4-bromophenylthio, methylamino, methylthio, ethylthio, n-propylthio, n-butylthio, n-pentylthio, n-hexylthio, 2-fluorophenylthio, 3-fluorophenylthio, 4-fluorophenylthio, 4-methylcumarinyl, naphtyl-2-thio, phenylthio, 4-nitrophenylthio, 2-aminophenylthio, 3-aminophenylthio, 4-aminophenylthio, benzylthio, phenylethylamino, 2-methoxyphenylthio, 3-methoxyphenylthio, 4-methoxyphenylthio, isopropylthio, benzimidazolyl-2-thio, 2-hydroxyethylthio, 2-aminoethylthio, pyridinylthio, benzothiazolylthio, 2-methylphenylthio, 3-methylphenylthio, 4-methylphenylthio, 2-isopropylphenylthio, 4-isopropylphenylthio, 2,3,5,6-tetrafluorophenylthio, 4-hydroxyphenylthio, 2,4-dichlorophenylthio, methoxy, benzyloxy, cyclohexylamino, benzylamino, phenylseleno, 4-isopropyloxyphenylthio, 4-methylthiophenylthio, 6-aminohexylamino, 2,3-dichlorophenylthio, 2,5-dichlorophenylthio, 2,4-difluorophenylthio, 2,5-dimethoxyphenylthio, 2,5-dimethylthiophenylthio, 2,6-dimethylthiophenylthio, 2,6-dichlorophenylthio.

In another preferred embodiment of the invention, $R_1$ is H, Br, Cl, azido, 4-chlorophenylthio, methylamino, methylthio, 4-fluorophenylthio, 4-methylcumarinyl, naphtyl-2-thio, phenylthio, 4-nitrophenylthio, 2-aminophenylthio, benzylthio, n-hexylthio, phenylethylamino, 4-methoxyphenylthio, isopropylthio, benzimidazolyl-2-thio, 2-hydroxyethylthio, ethylthio, 2-aminoethylthio, pyridinylthio, benzothiazolylthio, 4-methylphenylthio, 3-methoxyphenylthio, 4-isopropylphenylthio, 2,3,5,6-tetrafluorophenylthio, 4-hydroxyphenylthio, 2,4-dichlorophenylthio, methoxy, benzyloxy, cyclohexylamino, benzylamino, phenylseleno, 4-isopropyloxyphenylthio, 4-methylthiophenylthio, 6-aminohexylamino.

According to a further preferred embodiment of the invention, R1 is Cl, Br or S-aryl; preferably R1 is Cl, Br, 4-chlorophenylthio, 4-fluorophenylthio, naphtyl-2-thio, phenylthio, 4-nitrophenylthio, 4-methoxyphenylthio, pyridinyl-2-thio, 4-methylphenylthio, 4-isopropylphenylthio, 2,3,5,6-tetrafluoro-phenylthio, 4-hydroxyphenylthio, or 2,4-dichloro-phenylthio; and more preferably R1 is 4-chlorophenylthio, 4-fluorophenylthio, 4-methoxyphenylthio, 4-methylphenylthio, 4-hydroxyphenylthio.

In a further preferred embodiment $R_2$ is H, halogen, azido, O-alkyl, S-alkyl; preferably $R_2$ is H, Cl, Br, I, O-alkyl, S-methyl; more preferably $R_2$ is H, Cl, Br, O-methyl, O-ethyl, O-propyl, O-butyl, O-isobutyl, S-methyl; and most preferably R2 is O-methyl, O-ethyl, O-propyl, O-butyl, O-isobutyl.

According to another preferred embodiment of the invention R2 is O-methyl.

$R_3$ is preferably amino, NH-alkyl, N-bisalkyl, NH-aryl, NH-alkyl-carbamoyl, N-bisalkyl-carbamoyl, amido-alkyl, amido-aryl, OH; more preferably $R_3$ is amino, NH-phenyl, NH-tert-butyl, NH-tert-butylcarbamoyl, NH-phenylcarbamoyl, NH-acetyl, NH-propionyl, NH-butyryl, NH-benzoyl, NH-benzyl, NH-phenylethyl, NH-phenylpropyl, N-bismethyl, N-bisethyl, OH; and most preferably $R_3$ is amino, NH-phenyl, NH-tert-butyl, NH-tert-butylcarbamoyl, NH-phenylcarbamoyl; NH-butyryl, NH-benzoyl, NH-benzyl, N-bismethyl, N-bisethyl, OH.

According to another preferred embodiment $R_3$ is amino, NH-phenyl, NH-tert-butyl, NH-tert-butylcarbamoyl, NH-benzoyl, N-bismethyl, OH, preferably R3 is amino, NH-tert-butyl.

According to a further preferred embodiment of the invention $R_4$ and $R_5$ are independently O(H) or S(H), preferably R4 and R5 are O(H).

Preferred compounds of the invention are listed in table 1 and 2. Preferably, the compound is selected from the group consisting of 8-bromo-2'-deoxyadenosine-3',5'-cyclic monophosphate; 8-(4-chloro-phenylthio)-2'-deoxyadenosine-3',5'-cyclic monophosphate; 8-(4-chloro-phenylthio)-$N^6$-phenyl-2'-deoxyadenosine-3',5'-cyclic monophosphate; 8-bromo-2'-O-methyladenosine-3',5'-cyclic monophosphate; 8-(4-chloro-phenylthio)-2'-O-methyladenosine-3',5'-cyclic monophosphate; 8-methylamino-2'-O-methyladenosine-3',5'-cyclic monophosphate; 8-methylthio-2'-O-methyladenosine-3',5'-cyclic monophosphate; 8-(4-fluoro-phenylthio)-2'-O-methyladenosine-3',5'-cyclic monophosphate; 8-(4-methyl-cumarinyl-7-thio)-2'-O-methyladenosine-3',5'-cyclic monophosphate; 8-(naphtyl-2-thio)-2'-O-methyladenosine-3',5'-cyclic monophosphate; 8-phenylthio-2'-O-methyladenosine-3',5'-cyclic monophosphate; 8-(4-nitro-phenylthio)-2'-O-methyladenosine-3',5'-cyclic monophosphate; 8-(2-amino-phenylthio)-2'-O-methyladenosine-3',5'-cyclic monophosphate; 8-benzylthio-2'-O-methyladenosine-3',5'-cyclic monophosphate; 8-n-hexylthio-2'-O-methyladenosine-3',5'-cyclic monophosphate; 8-phenylethylamino-2'-O-methyladenosine-3',5'-cyclic monophosphate; 8-(4-methoxy-phenylthio)-2'-O-methyladenosine-3',5'-cyclic monophosphate; 8-isopropylthio-2'-O-methyladenosine-3',5'-cyclic monophosphate; 8-(benzimidazolyl-2-thio)-2'-O-methyladenosine-3',5'-cyclic monophosphate; 8-(2-hydroxy-ethylthio)-2'-O-methyladenosine-3',5'-cyclic monophosphate; 8-ethylthio-2'-O-methyladenosine-3',5'-cyclic monophosphate; 8-(2-amino-ethylthio)-2'-O-methyladenosine-3',5'-cyclic monophosphate; 8-(pyridinyl-2-thio)-2'-O-methyladenosine-3',5'-cyclic monophosphate; 8-(benzothiazolyl-2-thio)-2'-O-methyladenosine-3',5'-cyclic monophosphate; 8-(4-methyl-phenylthio)-2'-O-methyladenosine-3',5'-cyclic monophosphate; 8-(3-methoxy-phenylthio)-2'-O-methyladenosine-3',5'-cyclic monophosphate; 8-(4-isopropyl-phenylthio)-2'-O-methyladenosine-3',5'-cyclic monophosphate; 8-(2,3,5,6-tetrafluoro-phenylthio)-2'-O-methyladenosine-3',5'-cyclic monophosphate; 8-(4-hydroxy-phenylthio)-2'-O-methyladenosine-3',5'-cyclic monophosphate; 8-(2,4-dichloro-phenylthio)-2'-O-methyladenosine-3',5'-cyclic monophosphate; 8-(4-chloro-phenylthio)-2'-(N,N-dimethyl)-carbamoyl-adenosine-3',5'-cyclic monophosphate; 8-methoxy-2'-O-methyladenosine-3',5'-cyclic monophosphate; 8-benzyloxy-2'-O-methyladenosine-3',5'-cyclic monophosphate; 8-bromo-2'-O-methyladenosine-3',5'-cyclic monophosphorothioate, Sp-isomer; 8-bromo-2'-O-methyladenosine-3'-5'-cyclic monophophorothioate, Rp-isomer, 8-(4-chloro-phenylthio)-2'-O-methyladenosine-3',5'-cyclic monophosphorothioate, Sp-isomer; 8-(4-chloro-phenylthio)-2'-O-methyladenosine-3',5'-cyclic monophosphorothioate, Rp-isomer; 8-bromo-2'-deoxyadenosine-3',5'-cyclic monophosphorothioate, Rp-isomer; 8-bromo-2'-deoxyadenosine-3',5'-cyclic monophosphorothioate, Sp-isomer; 8-(4-chloro-phenylthio)-2'-deoxyadenosine-3',5'-cyclic monophosphorothioate, Rp-isomer; 8-(4-chloro-phenylthio)-2'-deoxyadenosine-3',5'-cyclic monophosphorothioate, Sp-isomer; and 8-cyclohexylamino-2'-deoxyadenosine-3',5'-cyclic monophosphate; 8-chloro-2'-O-methyladenosine-3',5'-cyclic monophosphate; $N^6$-tert-butyl-8-(4-chloro-phenylthio)-2'-deoxyadenosine-3',5'-cyclic monophosphate; 5,6-Dichloro-1-β-D-ribofuranosyl-2'-O-methylbenzimidazole-3',5'-cyclic monophosphate.

Epac tolerates a lot of modifications in the adenine nucleobase. Accordingly, the present invention also embraces deaza-analogues of the compounds, which refer to analogues of the compounds as defined wherein the purine lacks one or more ring nitrogen atoms, such as, but not limited to 1-deaza-adenine, 3-deaza-adenine, 7-deaza-adenine, dideaza-adenines, and benzimidazole (FIG. 1).

According to another preferred embodiment of the invention, the deaza-analogue is a compound having the structural formula II:

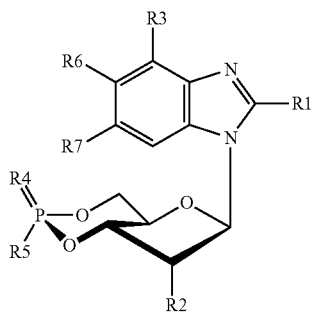

wherein
R1-R5 are as defined above, and wherein
R6 and R7 can be independently H, halogen, alkyl, nitro, amino, and/or alkoxy.
Preferably,
R1-R3 are as defined above;
R4 and R5 can be independently O or S; and
R6 and R7 can be independently F, Cl, Br or I, more preferably R6 and R7 are Cl.
In a preferred embodiment of the invention, R2 is O-alkyl.
According to a further preferred embodiment of the invention
R1 and R3 are hydrogen;
R2 is O-alkyl; and
R6 and R7 are Cl.

Preferred deaza-analogues according to the present invention are shown in FIG. 1. Preferably, the deaza-analogue is selected from the group consisting of 1-deaza-adenine analogues, 3-deaza-adenine analogues, 7-deaza-adenine analogues, 1,3-dideaza-adenine analogues, 1,7-dideaza-adenosine analogues and benzimidazole analogues, preferably 5,6-dichlorobenzimidazole.

The invention further relates to the above compounds for modulating the activity of Epacs, and/or for discriminating between the Epac- and PKA-mediated signal transduction pathways, which may be useful, for instance, for research into the function of both pathways in human physiology and pathology.

According to the invention, "modulating" refers to any alteration of the activity of Epacs, i.e. both activation and inhibition of Epacs, both in vitro and in vivo. The compounds according to the invention thus may have both a (partial) agonistic and a (partial) antagonistic activity.

In addition, the invention relates to pharmaceutical compositions comprising one or more of the compounds of the invention and one or more pharmaceutically acceptable excipients. Excipients are substantially inert substances that may be combined with one or more active compounds to facilitate administration of the composition. Examples of excipients include carriers, diluents, and/or additives and the like.

In addition, the invention relates to the use of a compound having the structural formula I

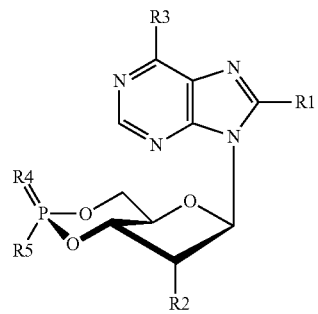

and/or deaza-analogues thereof, wherein R1-R5 are as defined above, as a medicament.

Furthermore, the invention relates to the use of compounds having the structural formula II:

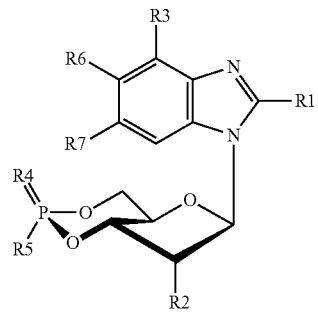

wherein R1-R7 are as defined above, as a medicament.

The invention further relates to the use of said compounds for the manufacture of a medicament for the treatment of human diseases, in particular for the treatment of cancer, chronic inflammation, thrombosis, diabetes mellitus, and mental disorders.

As will be clear to the skilled person, the compounds according to the present invention may further be labelled, according to well-known labeling techniques. For example, fluorescent dyes may be coupled to the compounds in order to localize the intracellular distribution of Epac proteins in living cells by means of confocal microscopy, or fluorescence correlation spectrometry with Epac, or fluorescence energy transfer studies with labelled Epac protein, or determination of Epac concentration in living cells. The fluorescent dye is preferably coupled, optionally via a spacer, to positions 6 and/or 8, since according to the invention substituents at these positions have been shown to be well excepted.

A spacer according to this invention refers to, but is not limited to, an aminoalkylamino moiety, or an aminoalkylthio moiety, or a thioalkylthio moiety, or a thioalkylcarboxy moiety, or an aminoalkylcarboxy moiety, or a thioureidoaminoalkylthio moiety, or an amino polyethyleneglycolamino moiety with 1 to 12 ethylene units.

Examples of suitable fluorescent dyes are fluorescein, rhodamine, anthraniloyl, N-ethylanthraniloyl, nitro-benzofurazanyl (NBD), Texas Red, CY™3, CY™5, CY™7 (CY™-family), EVOblue™10, EVOblue™30, EVOblue™90, EVOblue™100 (EVOblue™-family), BODIPY™-family, Alexa Fluor™-family.

The invention also relates to prodrugs of the compounds as defined above, wherein known functional moieties are coupled the compounds according to the invention, according to well known techniques. It is well known that such structures can enhance membrane-permeability and potency of the mother-compound 10-100 fold.

For example, the compounds may be transformed into bioactivatable prodrugs. For example, bioactivatable protecting groups may be coupled to the cyclic phosphate moiety, leading to significantly increased lipophilicity and bioavailability of the compounds of the invention. Examples for bioactivatable protection groups of the cyclic phosphate are acetoxymethyl, propionyloxymethyl, butyryloxymethyl, pivaloyloxymethyl, acetoxyethyl, acetoxy butyl, acetoxyisobutyl.

The compounds according to the present invention may also be transformed into chemically labile prodrugs according to well-known techniques. For example, alkyl or aryl groups may be coupled to the cyclic phosphate moiety, leading to significantly increased lipophilicity and bioavailability of the compounds of the invention. Examples for chemically labile protection groups of the cyclic phosphate are methyl, ethyl, propyl, benzyl, phenyl.

Examples of suitable labile prodrugs according to the invention are 8-Br-2'-O-Me-cAMP-benzyl ester (Example 14; FIG. 9A) and 8pCPT-2'-O-Me-cAMP-benzyl ester (Example 15; FIG. 9B). These compounds per se are inactive, but extremely membrane-permeable, leading to strongly increased intracellular concentrations. Upon hydrolysis of the benzyl ester, the mother compounds are released and able to modulate Epac.

The compounds according to the present invention may also be transformed into photolyzable (so-called caged) compounds according to well-known techniques. For example, caged groups may be coupled to the cyclic phosphate moiety, leading to compounds with significantly increased lipophilicity and bioavailability. Examples for caged groups of the cyclic phosphate are o-nitro-benzyl, 1-(o-nitrophenyl)-ethylidene, 4,5-dimethoxy-2-nitro-benzyl, 7-dimethylaminocoumarin-4-yl, 7-diethylamino-coumarin-4-yl.

DEFINITIONS

Listed below are the definitions of various terms and phrases used to describe the compounds of the present invention. These definitions apply to the terms as they are used throughout the specification.

Halogen refers to F, Cl, Br, and I.

Alkyl refers to an alkyl group, which is a substituted or unsubstituted, linear, branched or cyclic, saturated or unsaturated hydrocarbon moiety with 1 to 20 carbon atoms, with or without heteroatoms, including, but not limited to, methyl, ethyl, propyl, isopropyl, butyl, sec-butyl, tert-butyl, pentyl. Substituents include, but are not limited to, one or more halogen atoms, haloalkyl groups, (un)substituted aryl groups, (un)substituted heteroaryl groups, amino, nitro, cyano, azido, hydroxy, mercapto, keto, carboxy, methoxy.

Aryl refers to an aryl group, which is an unsubstituted or substituted aromatic or heteroaromatic hydrocarbon moiety, consisting of one or more aromatic or heteroaromatic rings with 3-8 ringatoms each. Substituents include, but are not limited to, one or more halogen atoms, haloalkyl groups, substituted or unsubstituted aryl groups, substituted or unsubstitued heteroaryl groups, amino, nitro, cyano, hydroxy, mercapto, carboxy, azido, methoxy, methylthio.

O-alkyl refers to an alkyl group, which is bound through an O-linkage, wherein the alkyl group is as defined above.

O-aryl refers to an aryl group, which is bound through an O-linkage, wherein the aryl group is as defined above.

S-alkyl refers to an alkyl group, which is bound through a S-linkage, wherein the alkyl group is as defined above.

S-aryl refers to an aryl group, which is bound through a S-linkage, wherein the aryl group is as defined above.

Se-alkyl refers to an alkyl group, which is bound through a Se-linkage, wherein the alkyl group is as defined above.

Se-aryl refers to an aryl group, which is bound through a Se-linkage, wherein the aryl group is as defined above.

NH-alkyl and N-bisalkyl refer to alkyl groups, which are bound through an N linkage, wherein the alkyl groups are as defined above.

NH-aryl and N-bisaryl refer to aryl groups, which are bound through an N linkage, wherein the aryl groups are as defined above.

Amido-alkyl refers to an alkyl group, which is bound through a NH—C(O)-alkyl linkage, wherein the alkyl group is as defined above.

Amido-aryl refers to an aryl group, which is bound through a NH—C(O)-aryl linkage, wherein the aryl group is as defined above.

Alkyl-carbamoyl refers to an alkyl group, which is bound through a —O—C(O)—NH-alkyl linkage, wherein the alkyl group is as defined above.

According to the present invention, the letter "p" stands for "para" (position 4) in the benzene ring, and "m" stands for "meta" (or position 3) in the benzene ring.

In the chair form of saturated six-membered rings, bonds to ring atoms, and the molecular entities attached to such bonds, are termed "axial" or "equatorial" according to whether they are located about the periphery of the ring ("equatorial"), or whether they are orientated above and below the approximate plane of the ring ("axial"). Due to the given stereochemistry of the cyclic phosphate ring, the axial position can only be above the approximate plane of the ring.

In the natural molecule cyclic AMP (cAMP), both $R_4$ and $R_5$ are oxygen, and the double bond is "distributed or dislocated" between both atoms. In water at physiological pH, the compound has a negative charge between both oxygens, and a corresponding cation, such as $H^+$ or $Na^+$. The structural formula is therefore often written with one double bond to oxygen and one single bond to a hydroxyl group, while it is of no importance whether the double bond goes to the axial oxygen $(R_4)'$ or the equatorial oxygen $(R_5)$. This is indicated by O(H) and S(H) in the definition of $R_4$ and $R_5$. This means that $R_4$ and $R_5$ could be either O or S or OH or SH, depending on the location of the double bond.

The situation changes, however, if one of the oxygen atoms is exchanged for a different group, e.g. sulphur. The phosphorus atom is now chiral and has four different ligands resulting in two stereoisomeric forms, the axial and equatorial isomers. If the sulphur is in the axial position $(R_4)$, the isomer may also be named the "Sp" isomer (from R/S nomenclature, and "p" for phosphorus), and if it is in the equatorial position $(R_5)$, the isomer may also be named the Rp-isomer. However, not all axial (equatorial) isomers will have a R(S) configuration, since this depends on the chemical nature of the substituents.

It is noted that all stereoisomeric forms of the compounds of the invention, i.e. axial and equatorial isomers, and Rp and Sp isomers, are embraced by the present invention.

Suitable examples of salts of the phosphate moiety of the compounds according to the invention are Li, Na, K, Ca, Mg or $NH_4$, and tetra-alkylammonium, trialkylammonium, dialkyammonium, alkylammonium, e.g. tetrabutylammonium, triethylammonium, trimethylammonium, diethylammonium, octylammonium and cetyltrimethylammonium. Alternatively, the free acid (H) form of the phosphate moiety is a suitable form for the compounds according to the invention.

It should be understood that solvates (e.g. hydrates) of the compounds are also within the scope of the present invention. Methods of salvation are generally known in the art.

The invention is further illustrated by the following Examples and Figures, describing preferred embodiments of the present invention, which are, however, not intended to limit the invention in any way.

FIG. 1 shows some formulas of deaza-analogues of the compounds of the invention.

FIG. 2 demonstrates the alignment of the cAMP-binding domains of PKA, Epac, olfactory channels, pacemaker channels, and the bacterial CAP protein.

Figure 6:
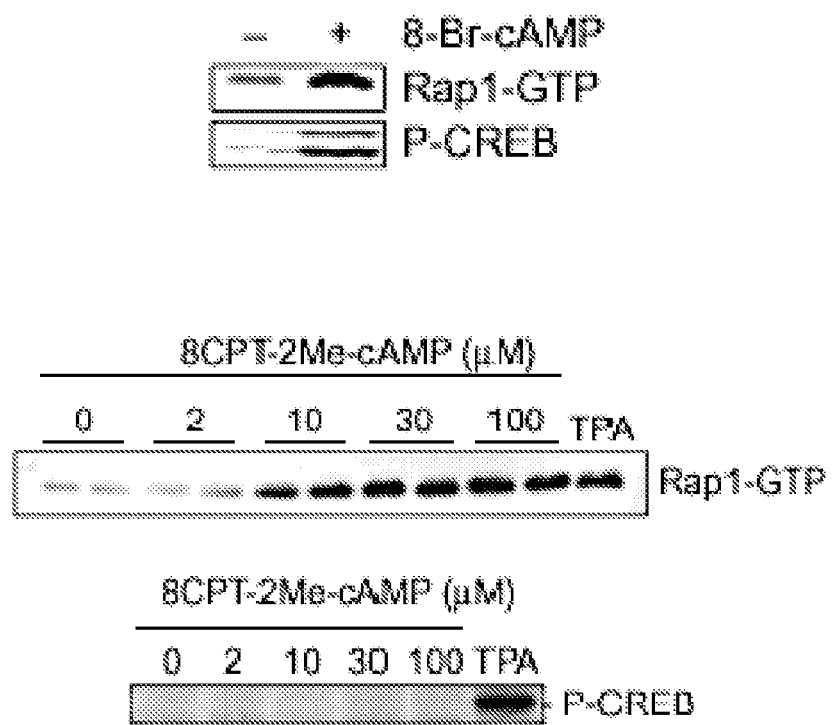

FIG. 6 shows that 8-pCPT-2'-O-Me-cAMP activates Rap1, but not PKA, in vivo. Upper panel: NIH3T3-A14-Epac1 cells were treated for 15 min with 8-Br-cAMP, and cell lysates were analyzed for activation of Rap1 and phosphorylation of CREB. Lower panel: NIH3T3-A14-Epac1 cells were treated in duplicate for 15 min with increasing concentrations of 8-pCPT-2'-O-Me-cAMP. Cells were lysed and equal amounts of cell lysate were incubated with precoupled GST-RalGDS-RBD and Rap1 was assayed by immunoblotting with Rap1 antibody. Phosphorylation of cAMP responsive element binding protein (CREB) in corresponding cell lysates was analyzed using a phospho-specific CREB antibody.

Figure 7:
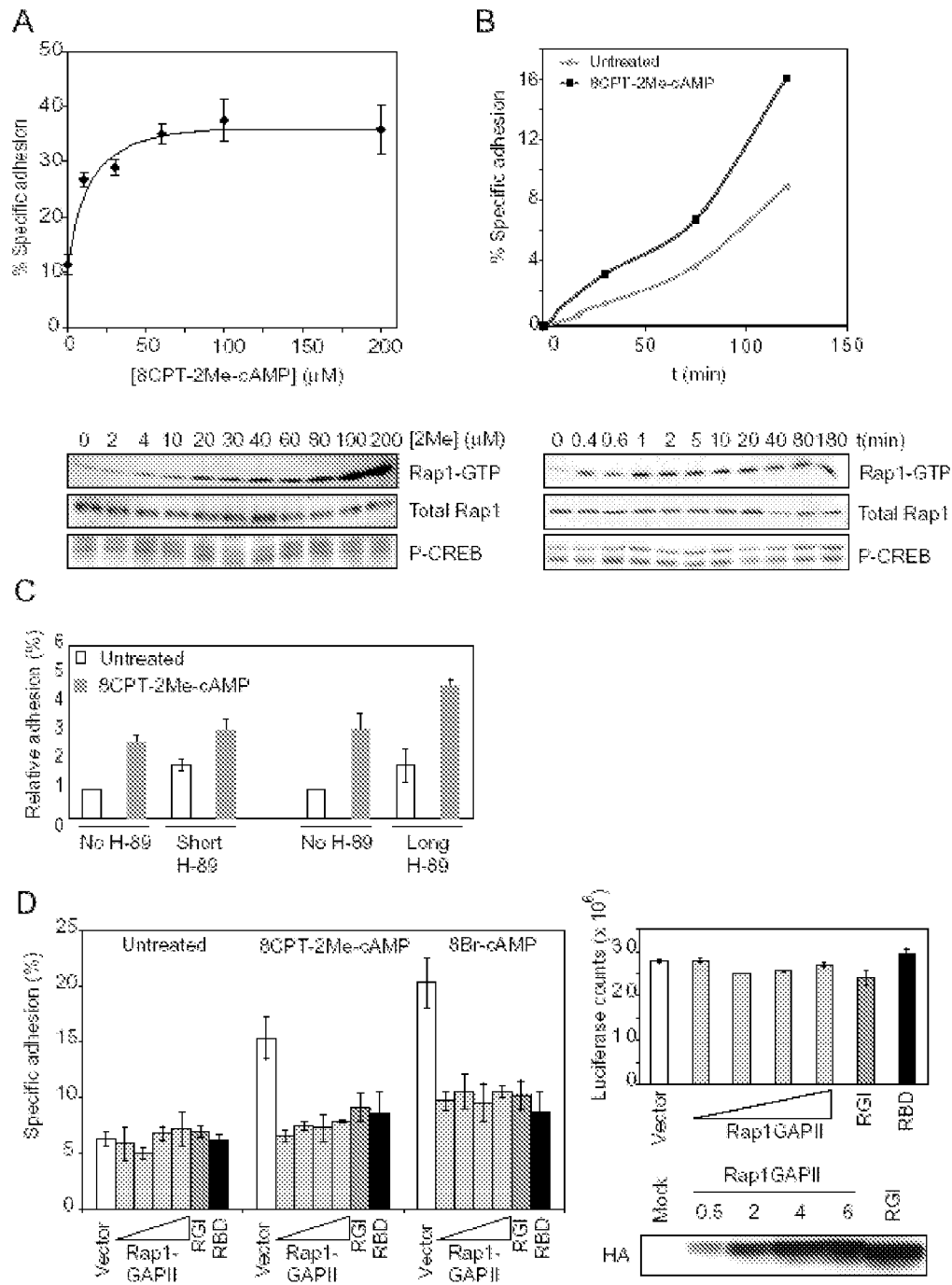

FIG. 7 shows that 8-pCPT-2'-O-Me-cAMP induces cell adhesion via Epac and Rap1. A: 8-pCPT-2'-O-Me-cAMP stimulates cell adhesion. Upper panel: quantification of Ovcar3 cells adhering to fibronectin after treatment with increasing concentrations of 8-pCPT-2'-O-Me-cAMP. Lower panel: Ovcar3 cells were treated with increasing concentrations of 8-pCPT-2'-O-Me-cAMP for 15 min, cells were lysed and analyzed for activation of Rap1 (upper blot) and CREB (lower blot). Total Rap1 levels are shown (middle blot). B: 8-pCPT-2'-O-Me-cAMP increases the rate of cell adhesion. Upper panel: quantification of Ovcar3 cells adhering to fibronectin at various time points. Lower panel: cells were treated with 60 µM 8-pCPT-2'-O-Me-cAMP for the indicated times. Cell lysates were analyzed for activation of Rap1 (upper blot) and CREB (lower blot). Total levels of Rap1 in cell lysates are shown (middle blot). C: Ovcar3 cells were either pre-incubated at 37° C. for 30 min with the PKA inhibitor H-89 (10 µM) 30 min prior to seeding onto the wells ('Short') or H-89 was added 30 min prior to trypsinization and during the recovery period ('Long') and seeded onto wells in the absence or presence of 8-pCPT-2'-O-Me-cAMP (100 µM). Cells were allowed to adhere for 1 h. D, cAMP-induced adhesion to fibronectin is blocked by inhibitors of Rap1. Left panel: Ovcar3 cells were transiently transfected with either mock DNA, increasing concentrations of HA-Rap1GAP II (0.5, 1, 2 or 6 µg, respectively), HA-Rap1GAPI (6 µg) or HA-RBD of RalGDS (6 µg), respectively. Cells were treated with 8-Br-cAMP or 8-pCPT-2'-O-Me-cAMP and adhesion to fibronectin was determined. Right upper panel: luciferase counts of total input cells per well in the above experiment are shown. Right lower panel: expression of HA-Rap1GAPs in the above experiment is shown.

Figure 8:
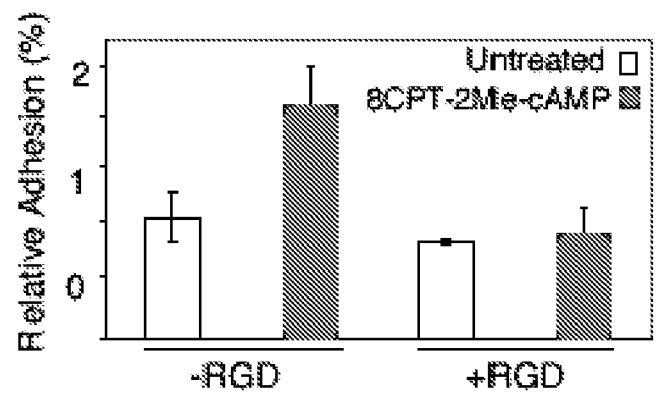
Figure 8:
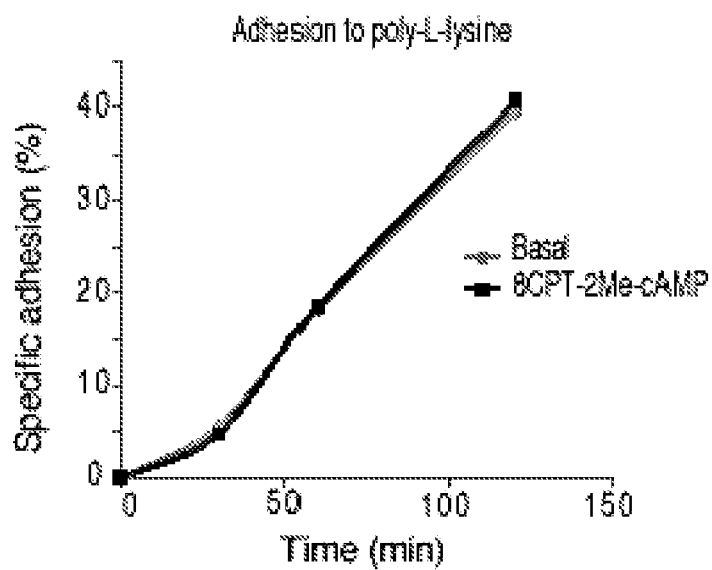

FIG. 8 shows that 8-pCPT-2'-O-Me-cAMP induces cell adhesion to fibronectin. Upper panel: a β1 integrin-blocking peptide containing the RGD sequence present in fibronectin inhibits 8-pCPT-2'-O-Me-cAMP-induced cell adhesion. Ovcar3 cells were pre-treated for 20 minutes with RGD-peptide (100 µM) where indicated, and seeded in wells with or without 8-pCPT-2'-O-Me-cAMP. Cells were allowed to adhere for 1 h. Lower panel: 8-pCPT-2'-O-Me-cAMP does not increase the rate of cell adhesion to poly-L-lysine. Ovcar3 cells were seeded onto poly-L-lysine-coated plates. At various time points, adherent cells were quantified.

Figure 9:
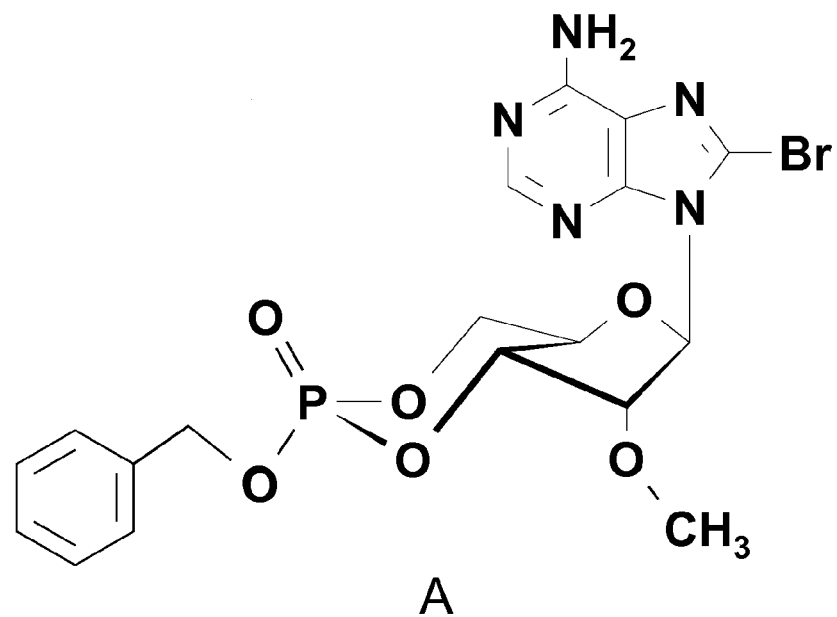
Figure 9:
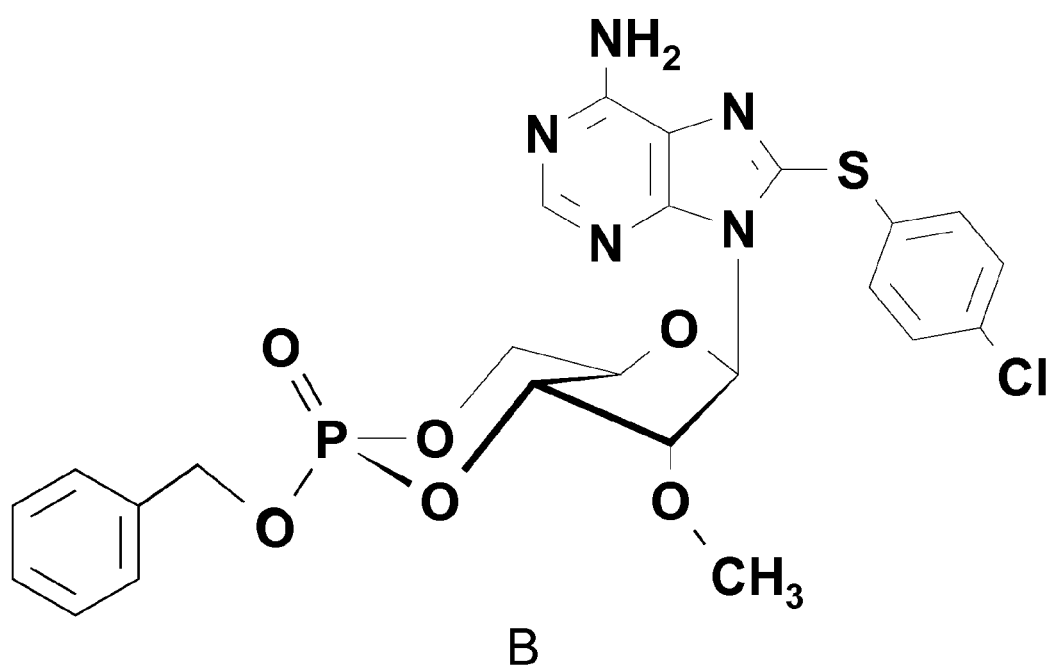

FIG. 9 shows two examples of so-calles prodrug forms of the compounds of the invention. A: 8-Br-2'-O-Me-cAMP-benzyl ester; B: 8pCPT-2'-O-Me-cAMP-benzyl ester.

EXAMPLES

By comparing the amino acid sequences of the cAMP binding domains of Epac with other cNMP binding domains described in literature, including the cAMP domains of PKA, olfactory and pacemaker channels and the bacterial CAP protein, it was found that the highly conserved glutamate, which makes the hydrogen bonding with the 2'-OH of the ribose group of cAMP (5), was absent in the cAMP binding domain of Epac1 and in the high affinity cAMP binding domain-B of Epac2 (FIG. 2).

It was thus hypothesized that this 2'-OH group, which is absolutely required for high affinity binding of cAMP to the cAMP binding domain of PKA, might not be required for efficient binding to and activation of Epac.

Accordingly, a large number of compounds were synthesized and tested (synthesis according to Genieser et al. (6), or modified according to Kataoka et al. (7), or Miller et al. (8).

Example 1

8-Bromo-2'-O-methyladenosine-3',5'-cyclic monophosphate (8-Br-2'-O-Me-cAMP)

A. Synthesis is performed as has already been described principally by Genieser et al.(6). Briefly, 1.8 g (5 mmoles) of 8-bromo-2'-O-methyladenosine are dissolved in 40 mL of triethyl phosphate and cooled in an ice bath. During gentle stirring, 915 µL (10 mmoles) of phosphoryl chloride are added at 0-5° C. The progress of reaction is monitored by high pressure liquid chromatography (RP-18, 6% isopropanol/10 mM triethyl ammonium phosphate buffer). After disappearance of starting nucleoside, the reaction mixture is poured into a solution of 60% acetonitrilel water and 0.008 M potassium hydroxide, followed by neutralisation with hydrochloric acid and evaporation to dryness. The residue is purified by means of column liquid chromatography using silica-based reversed phase material (Merck LiChroprep® RP-18). First elution with 100 mM $NaH_2PO_4$ is performed, then with 100% water. Finally, the product is eluted with 2% isopropanol/water. The product containing fractions are collected and evaporated. 671 mg (1.51 mmoles) 8-Br-2'-O-methyl-cAMP, sodium salt, are isolated with a purity >98% (yield: 30%).

B. Synthesis of 8-Br-2'-O-methyl-cAMP is also performed by a modified direct alkylation of 8-Br-cAMP, as has already been described in principle by Kataoka et al. (7). 11 g (26.96 mmoles) of 8-Br-cAMP, free acid (BIOLOG Life Science Institute, Bremen, Germany) and 6.048 g (108 mmoles) KOH pellets are dissolved in 100 mL deionized water by means of stirring at room temperature in a 500 mL flask. Afterwards, a solution of 6.78 g (108 mmoles) $CH_3I$ in 100 mL dioxan is added and the reaction mixture is stirred at room temperature until the starting material can no longer be detected by high pressure liquid chromatography (RP-18, 6% isopropanol/10 mM triethyl ammonium phosphate buffer). Excess $CH_3I$ is removed by repeated evaporation. The resulting raw product is dissolved in water and neutralized with 1 N HCl, and 8-Br-2'-O-methyl-cAMP is purified by means of column liquid chromatography using silica-based reversed phase material (Merck LiChroprep® RP-18). First elution with 100 mM $NaH_2PO_4$ is performed, then with 100% water. Finally, the product is eluted with 2% isopropanol/water. The product-containing fractions are collected and evaporated. 5.019 g (11.3 mmoles) 8-Br-2'-O-methyl-cAMP, sodium salt, are isolated with a purity of >98% (yield: 42%).

Formula: $C_{11}H_{12}BrN_5O_6P.Na$ (MW: 444.12)
Formula: $C_{11}H_{12}BrN_5O_6P.H$ (MW: 422.13)
$^1$H-NMR (DMSO-$d_6$), δ3.39 (s, 3H, —$CH_3$), 3.70-4.10 (m, 3H, H4', H5'ax, H5'eq), 4.58-4.65 (m, 1H, H3'), 4.90-5.20 (m, 1H, H2'), 5.74 (s, 1H, H1'), 7.51 (broad s, 2H, —$NH_2$), 8.17 (s, 1H, H2); $^{31}$P-NMR (DMSO-$d_6$), δ-2.49 (s); ESI-MS pos. mode: m/z 422/424 (M+H)$^+$, neg. mode: m/z 420/422 (M–H)$^-$; UV-VIS (pH 7.0) $\lambda_{max}$ 264 nm (ε=17000).

Example 2

8-(4-Chlorophenylthio)-2'-O-methyladenosine-3',5'-cyclic monophosphate (8-pCPT-2'-O-Me-cAMP)

A. Synthesis of 8-pCPT-2'-O-methyl-cAMP is performed by nucleophilic substitution of 8-Br-2'-O-methyl-cAMP as has already been described by Miller et al. (8). Briefly, 800 mg (1.8 mmoles) 8-Br-2'-O-methyl-cAMP, sodium salt, and 1.44 g (10 mmoles) 4-chlorothiophenol were dissolved in 100 mL of 50% acetonitrile/water in a 250 mL flask and refluxed until the starting material is completely converted. The progress of reaction is monitored by high pressure liquid chromatography (RP-18, 55% methanol/10 mM triethyl ammonium formate buffer). The mixture is evaporated to dryness, redissolved in 10% acetonitrile/water, and purified by means of column liquid chromatography using silica-based reversed phase material (Merck LiChroprep® RP-18). First, elution with 100 mM $NaH_2PO_4$ is performed, then with 100% water. Finally, the product is eluted with 8% isopropanol/water. The product-containing fractions are collected and evaporated. 741 mg (1.46 mmoles) 8-pCPT-2'-O-methyl-cAMP, sodium salt, are isolated with a purity of >99% (yield: 81%).

B. Synthesis of 8-pCPT-2'-O-methyl-cAMP is also performed by a modified direct alkylation of 8-pCPT-cAMP as has already been described by Kataoka et al. (7). 300 mg (0.608 mmoles) 8-pCPT-cAMP, free acid (BIOLOG Life Science Institute, Bremen, Germany) and 0.14 g (2.5 mmoles) KOH pellets are dissolved in 25 mL deionized water by means of stirring at room temperature in a 100 mL flask. Afterwards, a solution of 157 mg (2.5 mmoles) methyl iodide in 25 mL dioxan is added and the reaction mixture is stirred at room temperature until the starting material can no longer be detected by high pressure liquid chromatography (RP-18, 55% methanole/10 mM triethyl ammonium formate buffer). Excess $CH_3I$ is removed by repeated evaporation. The resulting raw product is dissolved in water, neutralized with 1 N HCl and purified by means of column liquid chromatography using silica-based reversed phase material (Merck LiChroprep® RP-18) Elution with 100 mM $NaH_2PO_4$ is first performed, then with 100% water. Finally, the product is eluted with 8% isopropanol/water. The product-containing fractions are collected and evaporated. 83 mg (0.163 mmoles) 8-pCPT-2'-O-methyl-cAMP, sodium salt, are isolated with a purity of >99% (yield: 27%).

Formula: $C_{17}H_{16}ClN_5O_6PS.Na$ (MW: 507.83)
Formula: $C_{17}H_{16}ClN_5O_6PS.H$ (MW: 585.85)
$^1$H-NMR (DMSO-$d_6$) β3.26 (s, 3H, —$CH_3$), 3.65-4.05 (m, 3H, H4', H5'ax, H5'eq), 4.51 (d, 1H, H2'), 4.90-5.0 (m, 1H, H3'), 5.94 (s, 1H, H1'), 7.30-7.45 (m, 4H, phenyl ring), 7.53 (br s, 2H, —$NH_2$), 8.19 (s, 1H, H2); $^{31}$P-NMR (DMSO-$d_6$) β-2.45 (s); ESI-MS pos. mode: m/z 486 (M+H)$^+$, 508 (M+Na)$^+$, neg. mode: m/z 484 (M–H)$^{31}$; UV-VIS (pH 7.0) $\lambda_{max}$ 282 nm (ε=16000).

Figure 1:
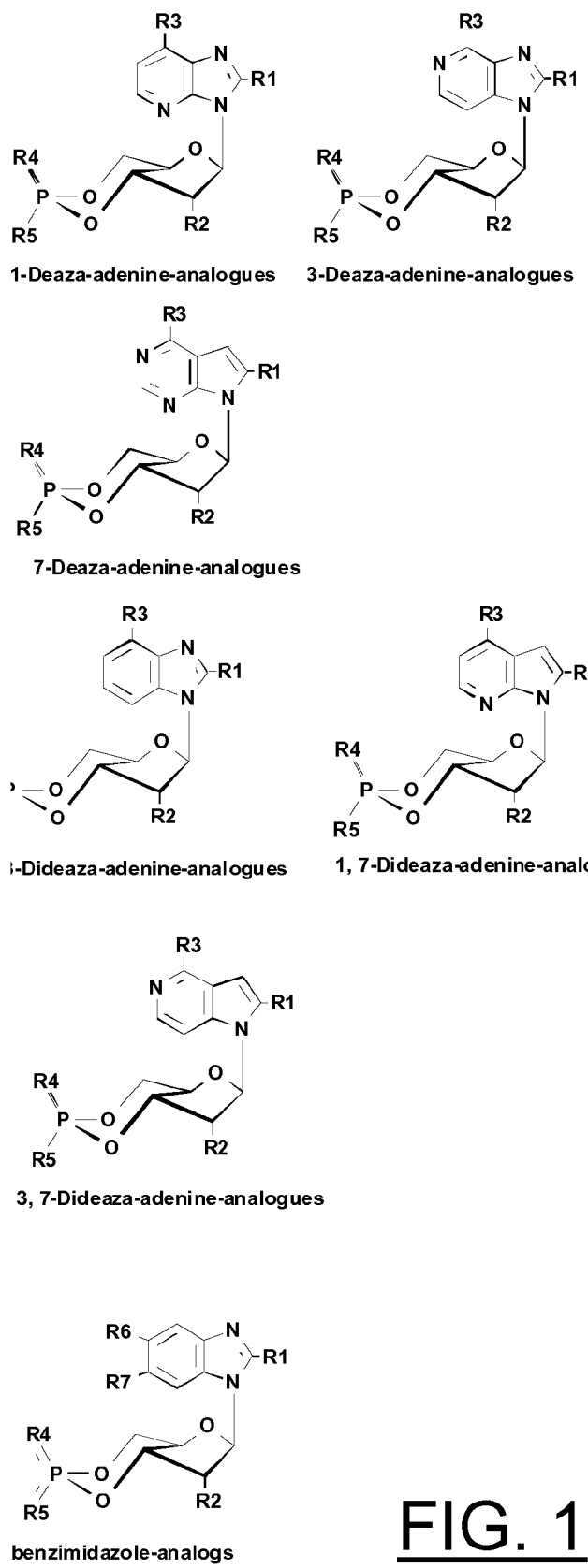
Figure 3:
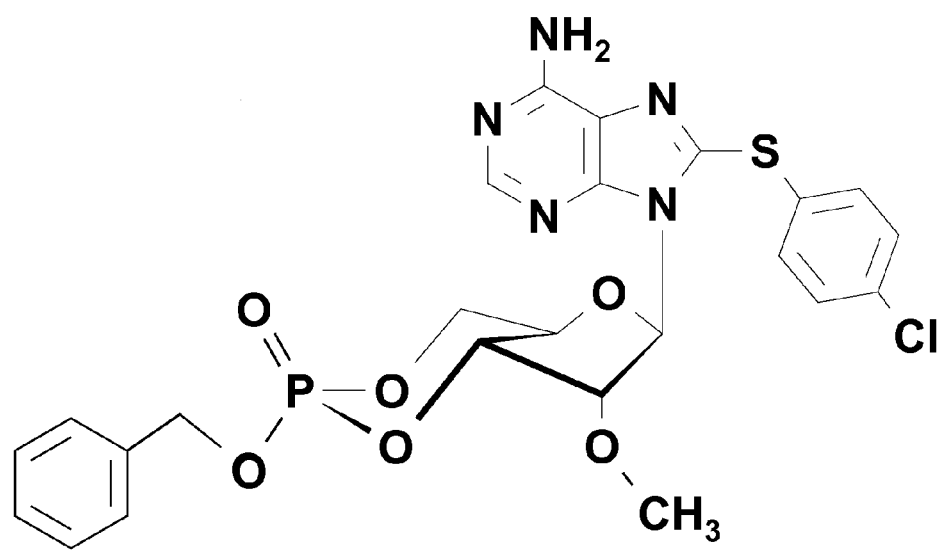
FIG. 3 shows the molecular structure of 8-pCPT-2'-O-Me-cAMP, a preferred compound of the invention.
Figure 4:
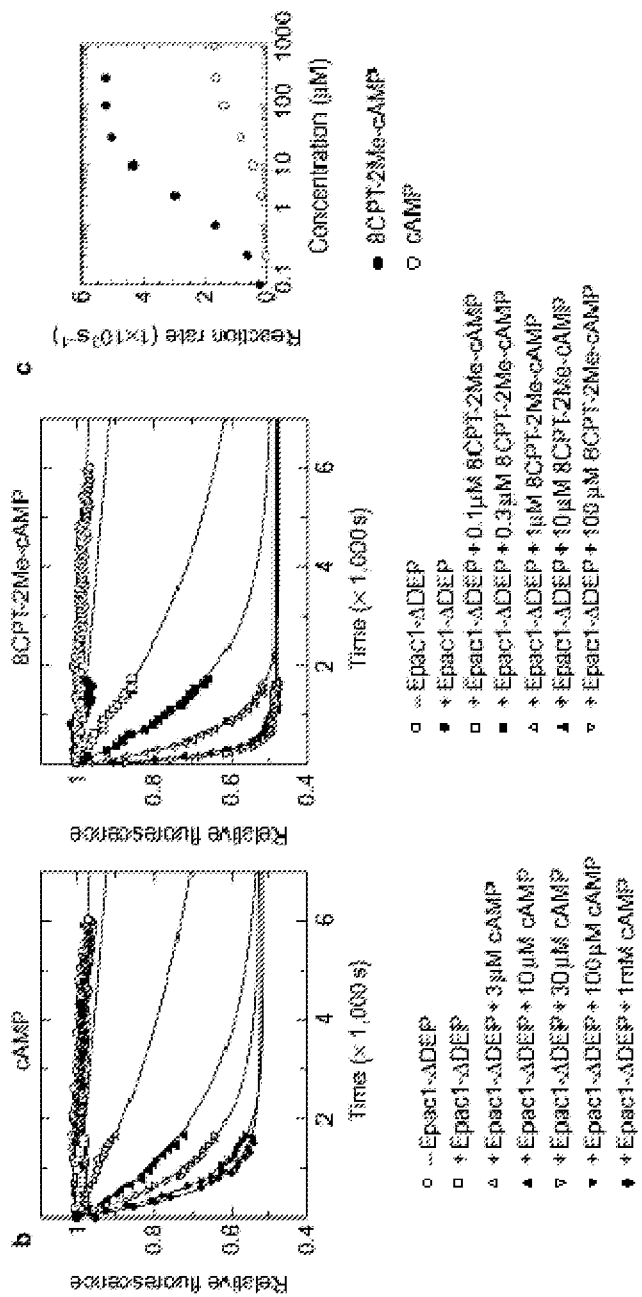
FIG. 4 shows in vitro activation of Epac1. Rap1 loaded with fluorescent Mant-GDP in the presence of a 100-fold excess of GTP was incubated with or without Epac1-ΔDEP in the presence of increasing concentrations of either cAMP (left panel) or 8-pCPT-2'-O-Me-cAMP (middle panel); the right panel shows the in vitro reaction rates of Epac for cAMP and 8-pCPT-2'-O-Me-cAMP.
Figure 5:
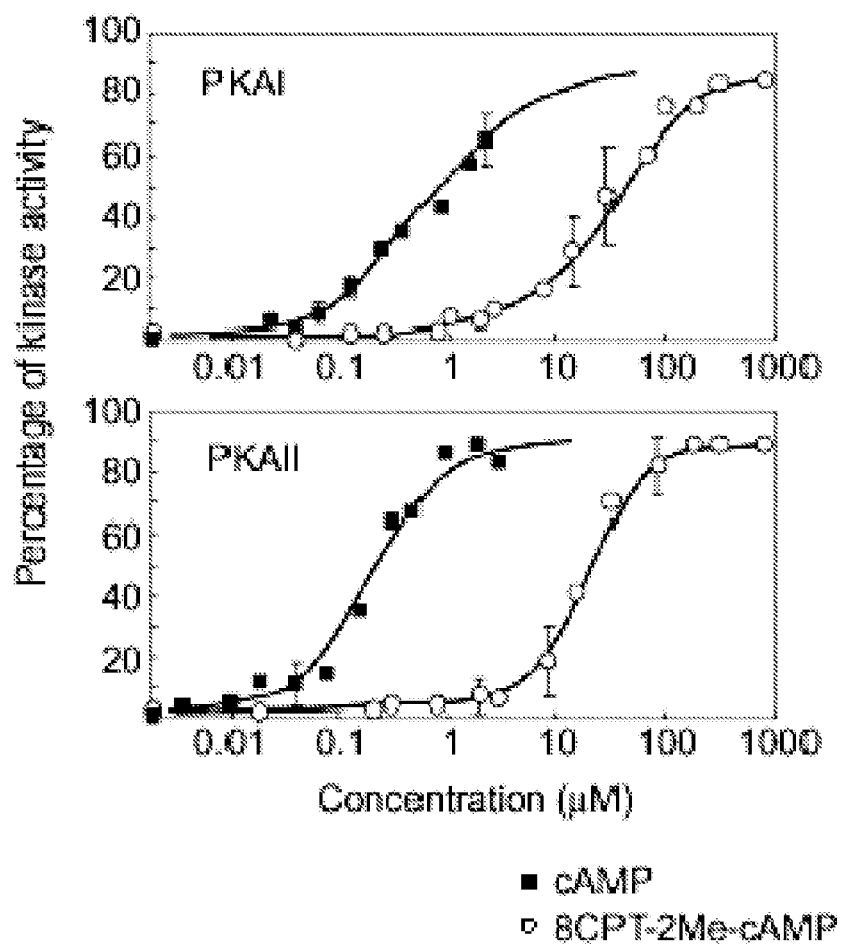
FIG. 5 shows the in vitro PKA activity of either type I holoenzyme (PKAI) or type II holoenzyme (PKAII) at increasing concentrations of either cAMP or 8-pCPT-2'-O-Me-cAMP.

This novel 8-pCPT-2'-O-Me-cAMP (FIG. 3) appeared to be a very efficient activator of Epac1 in vitro. Half-maximal activation of Epac1 was observed at 2.2 µM 8-pCPT-2'-O-Me cAMP compared to 30 µM for cAMP (FIG. 4). Interestingly, 8-pCPT-2'-O-Me-cAMP binding to Epac1 results in a three-fold higher maximal activity than cAMP, showing that 8-pCPT-2'-O-Me-cAMP is a much more potent allosteric regulator of Epac1 than cAMP. In contrast, the ability of 8-pCPT-2'-O-Me-cAMP to activate the type I and type II holoenzyme of PKA was greatly impaired compared to cAMP (FIG. 5).

These in vitro results indicated that 8-pCPT-2'-O-Me-cAMP may also be a very potent compound to discriminate between the Epac and the PKA signalling pathways in vivo. Therefore, 8-CPT-2'-O-Me-cAMP was tested in NIH3T3-A14-Epac1 cells for the activation of Epac, using Rap1 as a read-out, and of PKA, using phosphorylation of the common PKA substrate CREB 29 as a read-out. Importantly, whereas 8-Br-cAMP induced both the activation of Rap1 and the phosphorylation of CREB (FIG. 6, upper panel), 8-pCPT-2'-O-Me-cAMP induced the activation of Rap1 only. Dose-response experiments show that 8-pCPT-2'-O-Me-cAMP already activates Rap1 at a concentration of 10 µM (FIG. 6, lower panel), but did not induce CREB phosphorylation even at a concentration as high as 100 µM.

It can thus be concluded that 8-pCPT-2'-O-Me-cAMP is a highly specific and efficient activator of Rap1 and a very useful tool to discriminate between the PKA mediated and the Epac-Rap mediated signalling pathways. These results (including FIGS. 2, 4, 5, and 6) were published by Enserink et al. (9).

In functional assays, 8-pCPT-2'-O-Me-cAMP appeared to induce integrin-mediated cell adhesion through Epac and Rap1. Cytomegalovirus-luciferase-transfected ovarian carcinoma cells (Ovcar3), that express the β1 integrin chain involved in binding to fibronectin, were detached with trypsin and allowed to re-express cell surface markers. The cells were seeded onto fibronectin-coated plates in the presence or absence of 8-pCPT-2'-O-Me-cAMP and the amount of cells that adhered after a certain period of time was quantified. 8-pCPT-2'-O-Me-cAMP enhanced cell adhesion to fibronectin and induced Rap1 activation at comparable concentrations (EC50~30 µM; FIG. 7A). Even at a concentration of 200 µM, 8-pCPT-2'-O-Me-cAMP did not induce CREB phosphorylation. In a time-course analysis, we noted that increased adhesion was already observed after 30 minutes, which correlated with a rapid and sustained Rap1 activation (FIG. 7B). As expected, the induction of adhesion and activation of Rap1 were insensitive to the PKA inhibitor H-89 (FIG. 7C). However, even low levels of Rap1GAPII completely inhibited cAMP-induced adhesion of Ovcar3 cells to fibronectin (FIG. 7D, left plot). Furthermore, the Rap1-inhibitory proteins Rap1GAPI and Ras-binding domain (RBD) of Ral guanine nucleotide dissociation stimulator (RalGDS) also inhibited adhesion to fibronectin (FIG. 7D, left plot). Transfection of cells with Rap1GAPS or RBD of RalGDS did not affect luciferase expression (FIG. 7D, right plot).

To investigate whether 8-pCPT-2'-O-Me-cAMP-induced cell adhesion is mediated by integrins, Ovcar3 cells were pre-treated with the β1-integrin-binding arginine, glycine, aspartic acid (RGD) peptide. Peptides containing the RGD amino acid sequence motif bind to β1 integrins and have been shown to block fibronectin binding in ovarian carcinoma cells (10). Indeed, 8-pCPT-2'-O-Me-cAMP-induced attachment to fibronectin was abolished in the presence of the RGD peptide (FIG. 8). 8-pCPT-2'-O-Me-cAMP did not increase the integrin-independent adhesion of Ovcar3 cells to poly-L-lysine (FIG. 8). From these results, it was concluded that 8-pCPT-2'-O-Me-cAMP can induce integrin-mediated cell adhesion to fibronectin through the Epac-Rap1 signalling pathway. These results (including FIGS. 7 and 8) were published in Rangarajan et al. (11). Appropriate cell adhesion is necessary for numerous physiological processes and can be deregulated in many pathological conditions, e.g. cancer, chronic inflammation, and thrombosis.

Besides having an effect on adhesion, it was also demonstrated that in human pancreatic β-cells as well as in INS-1 insulin-secreting cells 8-pCPT-2'-O-Me-cAMP can induce mobilization of $Ca^{2+}$ from intracellular $Ca^{2+}$ stores via Epac-mediated $Ca^{2+}$-induced $Ca^{2+}$ release (CICR) and thereby induces exocytosis (12).

In summary, these findings suggest multiple therapeutic applications for cAMP analogues that specifically modulate the activity of Epacs, like 8-pCPT-2'-O-Me-cAMP, including treatment of cancer, chronic inflammation, thrombosis, and type-2 diabetes mellitus.

In addition, a large number of other new compounds were tested for their effect on Epac and PKA (Table 1 and 2).

Since phosphorothioate-modified cyclic nucleotides are known to be considerably protected from hydrolysis by cyclic nucleotide responsive phosphodiesterases (PDE), corresponding analogues were prepared as well, in order to obtain PDE-resistant tools, where necessary, e.g. for long term incubation experiments.

Example 3

8-Chloro-2'-O-methyladenosine-3',5'-cyclic monophosphate (8-Cl-2'-O-Me-cAMP)

Synthesis is performed as has already been described principally by Genieser et al. (6). Briefly, 789 mg (2.5 mmoles) 8-Chloro-2'-O-methyladenosine (BIOLOG Life Science Institute, Bremen, Germany) are dissolved in 20 mL of triethyl phosphate and cooled in an ice bath to 0-5° C. During gentle stirring and cooling, 457.5 µL (5 mmoles) of phosphoryl chloride are added at 0-5° C. Then the reaction mixture is stirred under cooling at 0-5° C. until the starting material can no longer be detected by high pressure liquid chromatography (RP-18, 6% isopropanole/10 mM triethyl ammonium phosphate buffer). After disappearence of starting nucleoside, the reaction mixture is poured into a solution of 60% acetonitrile/water and 0.008 M potassium hydroxide, followed by neutralisation with hydrochloric acid and evaporation to dryness. The residue is purified by means of column liquid chromatography using silica-based reversed phase material (Merck LiChroprep® RP-18). At first elution with 100 mM $NaH_2PO_4$ is performed, then with 100% water. Finally, the product is eluted with 2% isopropanole/water. The product containing fractions are collected and evaporated. 340 mg (0.85 mmoles) 8-Cl-2'-O-Me-cAMP, sodium salt are isolated with a purity >98% (yield: 34%)

Formula: $C_{11}H_{12}ClN_5O_6P.Na$ (MW: 399.69)
Formula: $C_{11}H_{12}ClN_5O_6P.H$ (MW: 377.67)
ESI-MS pos. mode: m/z 378 $(M+H)^+$, 400 $(M+Na)^+$, neg. mode: m/z 376 $(M-H)^-$; UV-VIS (pH 7.0) $\lambda_{max}$ 262 nm ($\epsilon$=17000).

Example 4

8-(4-Fluoro-phenylthio)-2'-O-methyladenosine-3',5'-cyclic monophosphate (8-pFPT-2'-O-Me-cAMP)

Synthesis of 8-pFPT-2'-O-Me-cAMP is performed by nucleophilic substitution of 8-Br-2'-O-methyl-cAMP as has already been described principally by Miller et al. (8). 30 µmoles 8-Br-2'-O-methyl-cAMP, sodium salt, and 300 µmoles 4-fluorothiophenol were dissolved in 1 mL of 50% acetonitrile/water in a 1.5 mL micro tube with screw cap and heated at 95° C. until the starting material is completely converted. The progress of reaction is monitored by high pressure liquid chromatography (RP-18, 6% isopropanole/10 mM triethyl ammonium formate buffer). The mixture is evaporated to dryness in a speed-vac centrifuge under reduced pressure under oil pump vacuum, redissolved in 0.5 mL 10% acetonitrile/water, and purified by means of semi-preparative hplc using silica-based reversed phase material (YMC ODS-A 120-11, RP-18). First, elution with 100 mM $NaH_2PO_4$ is performed, then with 100% water. Finally, the product is eluted with a gradient from 100% water to 100% acetonitrile. The product-containing fractions are collected and evaporated. 14 µmoles 8-pFPT-2'-O-Me-cAMP, sodium salt, are isolated with a purity of >97% (yield: 47%).

Formula: $C_{17}H_{16}FN_5O_6PS.Na$ (MW: 491.40)
Formula: $C_{17}H_{16}FN_5O_6PS.H$ (MW: 469.39)
ESI-MS pos. mode: m/z 470 $(M+H)^+$, 492 $(M+Na)^+$, neg. mode: m/z 468 $(M-H)^-$; UV-VIS (pH 7.0) $\lambda_{max}$ 283 nm.

Example 5

8-(4-Methoxy-phenylthio)-2'-O-methyladenosine-3',5'-cyclic monophosphate (8-pMeOPT-2'-O-Me-cAMP)

Synthesis of 8-pMeOPT-2'-O-Me-cAMP is performed by nucleophilic substitution of 8-Br-2'-O-methyl-cAMP as has already been described principally by Miller et al. (8). 30 µmoles 8-Br-2'-O-methyl-cAMP, sodium salt, were reacted with 300 µmoles 4-methoxythiophenol and the product was purified essentially as described in example 4. 10 µmoles 8-pMeOPT-2'-O-Me-cAMP, sodium salt, are isolated with a purity of >97% (yield: 33%).

Formula: $C_{18}H_{19}N_5O_7PS.Na$ (MW: 503.41)
Formula: $C_{18}H_{19}N_5O_7PS.H$ (MW: 481.43)
ESI-MS pos. mode: m/z 482 $(M+H)^+$, 504 $(M+Na)^+$, neg. mode: m/z 480 $(M-H)^-$; UV-VIS (pH 7.0) $\lambda_{max}$ 282 nm.

Example 6

8-(4-Methyl-phenylthio)-2'-O-methyladenosine-3',5'-cyclic monophosphate (8-pMPT-2'-O-Me-cAMP)

For synthesis of 8-pMPT-2'-O-Me-cAMP, 30 μmoles 8-Br-2'-O-methyl-cAMP, sodium salt, were reacted with 300 μmoles 4-methylthiophenol and the product was purified essentially as described in example 4. 11 μmoles 8-pMPT-2'-O-Me-cAMP, sodium salt, are isolated with a purity of >97% (yield: 37%).

Formula: $C_{18}H_{19}N_5O_6PS.Na$ (MW: 487.41)
Formula: $C_{18}H_{19}N_5O_6PS.H$ (MW: 465.43)
ESI-MS pos. mode: m/z 466 (M+H)$^+$, neg. mode: m/z 464 (M−H)$^−$; UV-VIS (pH 7.0) $\lambda_{max}$ 284 nm.

Example 7

8-(4-Hydroxy-phenylthio)-2'-O-methyladenosine-3',5'-cyclic monophosphate (8-pHPT-2'-O-Me-cAMP)

For synthesis of 8-pHPT-2'-O-Me-cAMP, 30 μmoles 8-Br-2'-O-methyl-cAMP, sodium salt, were reacted with 300 μmoles 4-hydroxythiophenol and the product was purified essentially as described in example 4. 16 μmoles 8-pHPT-2'-O-Me-cAMP, sodium salt, are isolated with a purity of >97% (yield: 53%).

Formula: $C_{17}H_{17}N_5O_7PS.Na$ (MW: 489.39)
Formula: $C_{17}H_{17}N_5O_7PS.H$ (MW: 467.40)
ESI-MS pos. mode: m/z 468 (M+H)$^+$, neg. mode: m/z 466 (M−H)$^−$; UV-VIS (pH.7.0) $\lambda_{max}$ 283 nm.

Example 8

8-Bromo-2'-O-methyladenosine -3',5'-cyclic monophosphorothioate, Rp-isomer (Rp-8-Br-2'-O-Me-cAMPS); 8-Bromo-2'-O-methyladenosine -3',5'-cyclic monophosphorothioate, Sp-isomer (Sp-8-Br-2'-O-Me-cAMPS)

Synthesis is performed as has already been described principally by Genieser et al.(13). Briefly, 0.9 g (2.5 mmoles) of 8-bromo-2'-O-methyladenosine are dissolved in 20 mL of triethyl phosphate. During gentle stirring, 457 μL (5 mmoles) of thiophosphoryl chloride are added. The progress of reaction is monitored by high pressure liquid chromatography (RP-18, 6% isopropanole/10 mM triethyl ammonium phosphate buffer). After disappearance of starting nucleoside, the reaction mixture is poured into a refluxing solution of 60% acetonitrile/water and 0.008 M potassium hydroxide, followed by neutralisation with hydrochloric acid and evaporation to dryness. The residue is purified by means of column liquid chromatography using silica-based reversed phase material (Merck LiChroprep® RP-18). First elution with 100 mM $NaH_2PO_4$ is performed, then with 100% water. Finally, the diastereomers (Rp and Sp) are eluted with a gradient from 0%-5% isopropanol/water. Subsequently, the separated diastereomers Rp- and Sp-8-Br-2'-O-Me-cAMPS are further purified by applying the same chromatographic system as described above. Product containing fractions are collected and evaporated.

181 μmoles Rp-8-Br-2'-O-Me-cAMPS, sodium salt, are isolated with a purity >98% (yield: 7.2%).

197 μmoles Sp-8-Br-2'-O-Me-cAMPS, sodium salt, are isolated with a purity >98% (yield: 7.9%).

Rp-8-Br-2'-O-Me-CAMPS
Formula: $C_{11}H_{12}BrN_5O_5PS.Na$ (MW: 460.19)
Formula: $C_{11}H_{12}BrN_5O_5PS.H$ (MW: 438.20)
ESI-MS pos. mode: m/z 438/440 (M+H)$^+$, 460/462 (M+Na)$^+$, neg. mode: m/z 436/438 (M−H)$^−$; 212/214 (8-Br-Ade-H)$^−$; UV-VIS (pH 7.0) $\lambda_{max}$ 264 nm ($\epsilon$=17000).

Sp-8-Br-2'-O-Me-cAMPS
Formula: $C_{11}H_{12}BrN_5O_5PS.Na$ (MW: 460.19)
Formula: $C_{11}H_{12}BrN_5O_5PS.H$ (MW: 438.20)
ESI-MS pos. mode: m/z 438/440 (M+H)$^+$, 460/462 (M+Na)$^+$, neg. mode: m/z 436/438 (M−H)$^−$; UV-VIS (pH 7.0) $\lambda_{max}$ 264 nm ($\epsilon$=17000).

Example 9

8-(4-Chloro-phenylthio)-2'-O-methyladenosine-3',5'-cyclic monophosphorothioate, Rp-isomer (Rp-8-pCPT-2'-O-Me-cAMPS)

Synthesis of Rp-8-pCPT-2'-O-Me-cAMPS is performed by nucleophilic substitution of Rp-8-Br-2'-O-methyl-cAMPS as has already been described principally by Miller et al. (8). 60 μmoles Rp-8-Br-2'-O-methyl-cAMPS, sodium salt, were reacted with 600 μmoles 4-chlorothiophenol in a 2 mL micro tube with screw cap and the product was purified essentially as described in example 4. 17 μmoles Rp-8-pCPT-2'-O-Me-cAMPS, sodium salt, are isolated with a purity of >98% (yield: 28%).

Formula: $C_{17}H_{16}ClN_5O_5PS_2.Na$ (MW: 523.90)
Formula: $C_{17}H_{16}ClN_5O_5PS_2.H$ (MW: 501.92)
ESI-MS pos. mode: m/z 502 (M+H)$^+$, 524 (M+Na)$^+$, neg. mode: m/z 500 (M−H)$^−$; WV-VIS (pH 7.0) $\lambda_{max}$ 282 nm ($\epsilon$=16000).

Example 10

8-(4-Chloro-phenylthio)-2'-O-methyladenosine-3',5'-cyclic monophosphorothioate, Sp-isomer (Sp-8-pCPT-2'-O-Me-cAMPS)

For synthesis of Sp-8-pCPT-2'-O-Me-cAMPS, 60 μmoles Sp-8-Br-2'-O-methyl-cAMPS, sodium salt, were reacted with 600 μmoles 4-chlorothiophenol and the product was purified essentially as described in example 9. 15 μmoles Sp-8-pCPT-2'-O-Me-cAMPS, sodium salt, are isolated with a purity of >96% (yield: 25%).

Formula: $C_{17}H_{16}ClN_5O_5PS_2.Na$ (MW: 523.90)
Formula: $C_{17}H_{16}ClN_5O_5PS_2.H$ (MW: 501.92)
ESI-MS pos. mode: m/z 502 (M+H)$^+$, 524 (M+Na)$^+$, neg. mode: m/z 500 (M−H)$^−$; UV-VIS (pH 7.0) $\lambda_{max}$ 282 nm (F = 16000).

Example 11

$N^6$-Mono-tert.-butyl-8- (4-chlorophenylthio) -2'-O-methyl-adenosine-3',5'-cyclic monophosphorothioate (6-MTB-8-pCPT-2'-O-Me-cAMP)

70 μmoles of 8-pCPT-2'-O-methyl-cAMP, sodium salt, is suspended in 3 ml of tert.-butylisocyanate and 500 μl of dry DMSO added. The flask is heated under reflux conditions at 150° C. for 1.5 hours. The progress of reaction is monitored by high pressure liquid chromatography (RP-18, 35% isopropanole/10 mM triethyl ammonium formiate buffer). The raw product is evaporated until a small liquid rest and purified on a reversed phase (RP 8) silica column using ion pair chromatography. The product containing fractions are pooled and desalted on reversed phase silica.

15 μmoles of 6-MTB-8-pCPT-2'-O-Me-cAMP, sodium salt, are isolated with a purity of >98% (yield: 21.4%).

Formula: $C_{21}H_{24}ClN_5O_6PS.Na$ (MW: 563.93)
Formula: $C_{21}H_{24}ClN_5O_6PS.H$ (MW: 541.95)

ESI-MS pos. mode: m/z 542 (M+H)$^+$, 564, (M+Na)$^+$, neg. mode: m/z 540 (M−H)$^−$; UV-VIS (pH 7.0) $\lambda_{max}$ 290 nm, sh 295 nm ($\epsilon$=25.000, calc.).

Example 12

N$^6$,N$^6$-Di-tert.-butyl-8-(4-chlorophenylthio) -2'-O-methyladenosine-3',5'-cyclic monophosphorothioate (6-DTB-8-pCPT-2'-O-Me-cAMP)

The product containing later fractions of the raw product from EXAMPLE 11 are pooled and evaporated. The product precipitates on the flask wall and can be collected by dissolution with methanol and subsequent evaporation of solvent to yield 5 µmoles of 6-DTB-8-pCPT-2'-O-Me-cAMP, sodium salt, wich are isolated with a purity of 96.5% (yield: 7%).

Formula: $C_{25}H_{32}ClN_5O_6PS\cdot Na$ (MW: 620.04)
Formula: $C_{25}H_{32}ClN_5O_6PS\cdot H$ (MW: 598.05)
ESI-MS pos. mode: m/z 599 (M+H)$^+$, 621 (M+Na)$^+$, neg. mode: m/z 597 (M−H)$^−$; UV-VIS (pH 7.0) $\lambda_{max}$ 295 nm ($\epsilon$=30.000 (calc.).

Example 13

N$^6$-Mono-tert.-butylcarbamoyl-8-(4-chlorophenylthio)-2'-O-methyl-adenosine-3',5'-cyclic monophosphorothioate (6-MBC-8-pCPT-2'-O-Me-cAMP)

50 µmoles of 8-pCPT-2'-O-methyl-cAMP, sodium salt, are dissolved in 1 ml of dry dimethylformamide (DMF) and 250 µl of tert.-butylisocyanate added. The flask is heated under reflux conditions at 80° C. for several hours. The progress of reaction is monitored by high pressure liquid chromatography (RP-18, 35% isopropanole/10 mM triethyl ammonium formiate buffer). After 2 hours another 250 µl of tert.-butylisocyanate are added. The raw product is evaporated until a small liquid rest and purified on a semi-preparative reversed phase (RP 8) silica column using the same ion pair chromatography system. The product containing fractions are pooled and desalted on reversed phase silica.

10 µmoles of 6-MBC-8-pCPT-2'-O-Me-cAMP, sodium salt, are isolated with a purity of >98% (yield: 20%).

Formula: $C_{22}H_{24}ClN_6O_7PS\cdot Na$ (MW: 605.95)
Formula: $C_{22}H_{24}ClN_6O_7PS\cdot H$ (MW: 583.97)
ESI-MS pos. mode: m/z 585 (M+H)$^+$, neg. mode: m/z 583 (M−H)$^−$; UV-VIS (pH 7.0) $\lambda_{max}$ 289 nm, sh 295 nm ($\epsilon$=25.000, calc.).

Example 14

8-Bromo-2'-O-methyladenosine-3',5'-cyclic monophosphate, benzyl ester (8-Br-2'-O-Me-cAMP-Bn)

Synthesis is performed as has already been described principally by Furuta et al. (14). Briefly, 93.8 µmoles of 8-Br-2'-O-Me-cAMP are dissolved in 900 µL acetonitrile and 100 µL DMF. After addition of 188 µmoles (43.5 mg) silver(I) oxide and 216 µmoles (25.7 µL) benzyl bromide the reaction mixture is stirred at 50° C. for 19 h. Progress of reaction is monitored by high pressure liquid chromatography (RP-18, 55% methanol/water). The silver(I) oxide is removed by filtration. The filtrate is evaporated to dryness in a speed-vac centrifuge under reduced pressure under oil pump vacuum, redissolved in 0.5 mL 50% methanol/water, and purified by means of semi-preparative hplc using silica-based reversed phase material (YMC ODS-A 120-11, RP-18). The product-containing fractions are collected and evaporated. 35 µmoles 8-Br-2'-O-Me-cAMP-Bn (21 µmoles of axial isomer and 14 µmoles of equatorial isomer) are isolated with a purity of >97% (yield: 37%).

Formula: $C_{18}H_{19}BrN_5O_6P$ (MW: 512.25)
ESI-MS pos. mode: m/z 512/514 (M+H)$^+$, neg. mode: m/z 510/512 (M−H)$^−$; UV-VIS (pH 7.0) $\lambda_{max}$ 264 nm ($\epsilon$=17000).

Example 15

8-(4-Chlorophenylthio)-2'-O-methyladenosine-3',5'-cyclic monophosphate, benzyl ester (8-pCPT-2'-O-Me-cAMP-Bn)

Synthesis is performed as has already been described principally by Furuta et al. (14). 114 µmoles of 8-pCPT-2'-O-Me-cAMP are dissolved in 900 µL acetonitrile and 100 µL DMF. After addition of 228 µmoles (52.8 mg) silver(I) oxide and 216 µmoles (25.7 µL) benzyl bromide the reaction mixture is stirred at 50° C. for 22 h. Progress of reaction is monitored by high pressure liquid chromatography (RP-18, 45% acetonitrile/water). The silver(I) oxide is removed by filtration and the resulting filtrate is evaporated to dryness in a speed-vac centrifuge under reduced pressure under oil pump vacuum, redissolved in 0.5 mL 50% acetonitrile/water, and purified by means of semi-preparative hplc using silica-based reversed phase material (YMC ODS-A 120-11, RP-18). The product-containing fractions are collected and evaporated. 9 µmoles 8-pCPT-2'-O-Me-cAMP-Bn (5 µmoles of axial isomer and 4 µmoles of equatorial isomer) are isolated with a purity of >98.5% (yield: 8%).

Formula: $C_{24}H_{23}ClN_5O_6PS$ (MW: 575.96)
ESI-MS pos. mode: m/z 576 (M+H)$^+$, neg. mode: m/z 574 (M−H)$^−$; UV-VIS (pH 7. 0) $\lambda_{max}$ 282 nm ($\epsilon$=16000).

TABLE 1

Structures of novel compounds according to the invention.

| Compound | Name | Chemical structure |
| --- | --- | --- |
| 2'-dcAMP 2'-deoxy-adenosine-3',5'-cyclic monophosphate | I-001 | 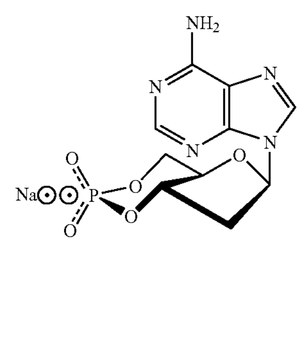 |

TABLE 1-continued

Structures of novel compounds according to the invention.

| Compound | Name | Chemical structure |
|---|---|---|
| 8-Br-2'-dcAMP<br>8-bromo-2'-deoxy-adenosine-3',5'-cyclic monophosphate | I-002 | 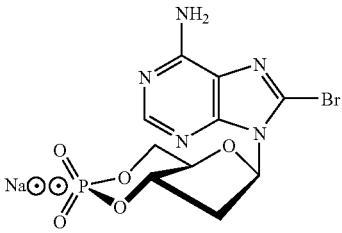 |
| 8-pCPT-2'-dcAMP<br>8-(4-chloro-phenylthio)-2'-deoxy-adenosine-3',5'-cyclic monophosphate | I-003 | 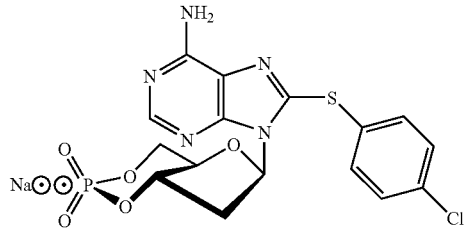 |
| 8-pCPT-6-Phe-2'-dcAMP<br>8-(4-chloro-phenylthio)-N$^6$-phenyl-2'-deoxy-adenosine-3',5'-cyclic monophosphate | I-004 | 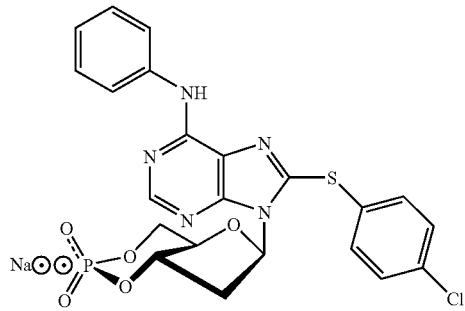 |
| 2'-O—Me-cAMP<br>2'-O-methyl-adenosine-3',5'-cyclic monophosphate | I-005 | 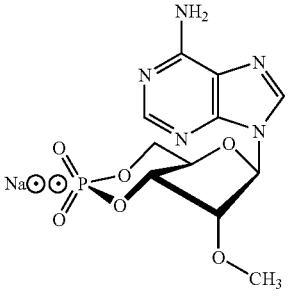 |
| 8-Br-2'-O—Me-cAMP<br>8-bromo-2'-O-methyl-adenosine-3',5'-cyclic monophosphate | I-006 | 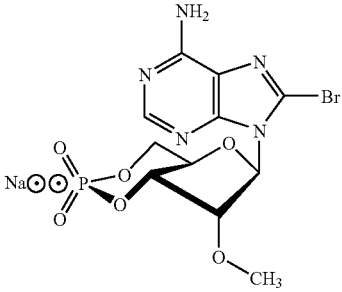 |

TABLE 1-continued

Structures of novel compounds according to the invention.

| Compound | Name | Chemical structure |
|---|---|---|
| 8-pCPT-2'-O—Me-cAMP<br>8-(4-chloro-phenylthio)-2'-O-methyl-adenosine-3',5'-cyclic monophosphate | I-007 | 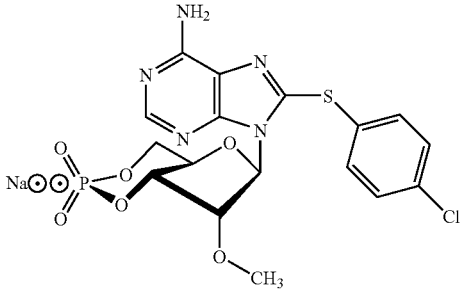 |
| 2'-O—Et-cAMP<br>2'-O-ethyl-adenosine-3',5'-cyclic monophosphate | I-008 | 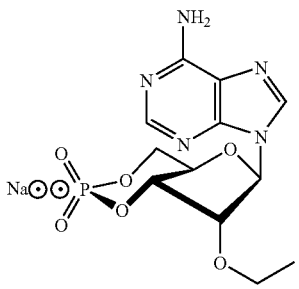 |
| 2'-O—Pr-cAMP<br>2'-O-propyl-adenosine-3',5'-cyclic monophosphate | I-009 | 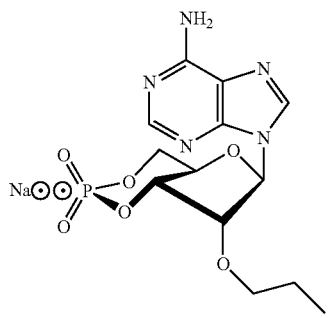 |
| 2'-O—Bu-cAMP<br>2'-O-n-butyl-adenosine-3',5'-cyclic monophosphate | I-010 | 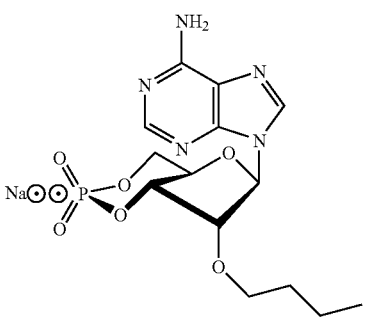 |
| 2'-O—iBu-cAMP<br>2'-O-isobutyladenosine-3',5'-cyclic monophosphate | I-011 | 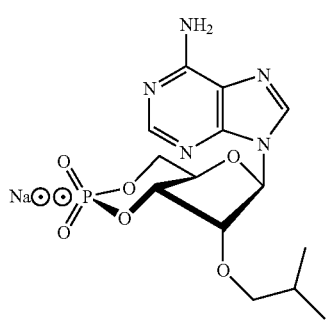 |

TABLE 1-continued

Structures of novel compounds according to the invention.

| Compound | Name | Chemical structure |
|---|---|---|
| 8-MA-2'-O—Me-cAMP<br>8-methylamino-2'-O-methyl-adenosine-3',5'-cyclic monophosphate | I-100 | |
| 8-MT-2'-O—Me-cAMP<br>8-methylthio-2'-O-methyl-adenosine-3',5'-cyclic monophosphate | I-101 | |
| 8-pFPT-2'-O—Me-cAMP<br>8-(4-fluoro-phenylthio)-2'-O-methyl-adenosine-3',5'-cyclic monophosphate | I-102 | |
| 8-MCT-2'-O—Me-cAMP<br>8-(4-methyl-cumarinyl-7-thio)-2'-O-methyladenosine-3',5'-cyclic monophosphate | I-103 | |
| 8-NT-2'-O—Me-cAMP<br>8-(naphtyl-2-thio)-2'-O-methyladenosine-3',5'-cyclic monophosphate | I-104 | |

TABLE 1-continued

Structures of novel compounds according to the invention.

| Compound | Name | Chemical structure |
|---|---|---|
| 8-PT-2'-O—Me-cAMP<br>8-phenylthio-2'-O-methyladenosine-3',5'-cyclic monophosphate | I-105 | 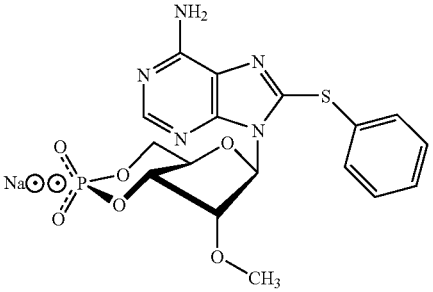 |
| 8-pNPT-2'-O—Me-cAMP<br>8-(4-nitro-phenylthio)-2'-O-methyladenosine-3',5'-cyclic monophosphate | I-106 | 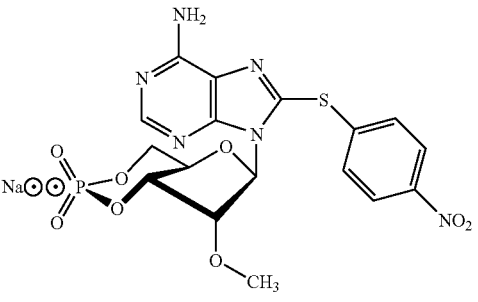 |
| 8-oAPT-2'-O—Me-cAMP<br>8-(2-amino-phenylthio)-2'-O-methyladenosine-3',5'-cyclic monophosphate | I-107 | 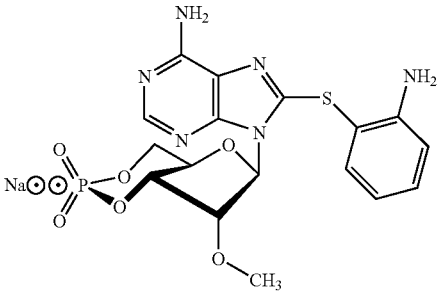 |
| 8-BnT-2'-O—Me-cAMP<br>8-benzylthio-2'-O-methyladenosine-3',5'-cyclic monophosphate | I-108 | 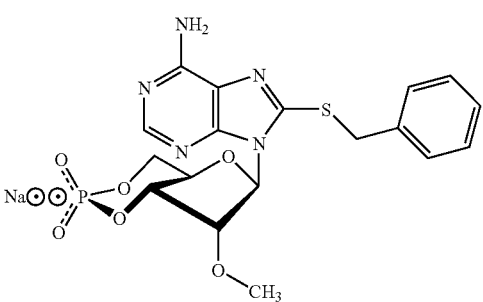 |
| 8-HT-2'-O—Me-cAMP<br>8-n-hexylthio-2'-O-methyladenosine-3',5'-cyclic monophosphate | I-109 | 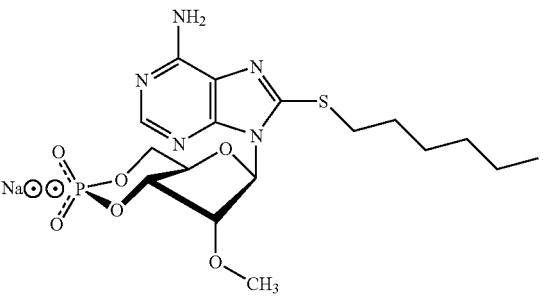 |

TABLE 1-continued

Structures of novel compounds according to the invention.

| Compound | Name | Chemical structure |
|---|---|---|
| 8-PhEA-2'-O—Me-cAMP<br>8-phenyl-ethylamino-2'-O-methyladenosine-3',5'-cyclic monophosphate | I-111 | 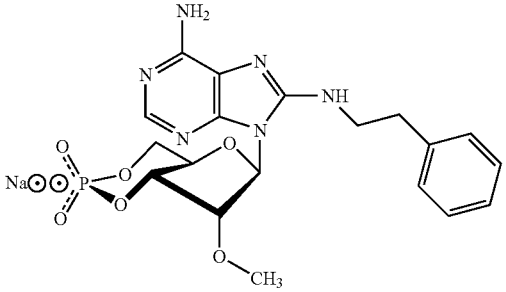 |
| 8-pMeOPT-2'-O—Me-cAMP<br>8-(4-methoxy-phenylthio)-2'-O-methyladenosine-3',5'-cyclic monophosphate | I-112 | 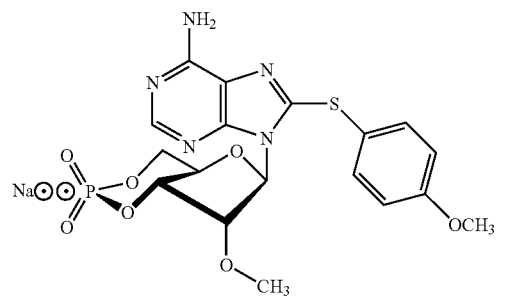 |
| 8-IPT-2'-O—Me-cAMP<br>8-iso-propylthio-2'-O-methyladenosine-3',5'-cyclic monophosphate | I-113 | 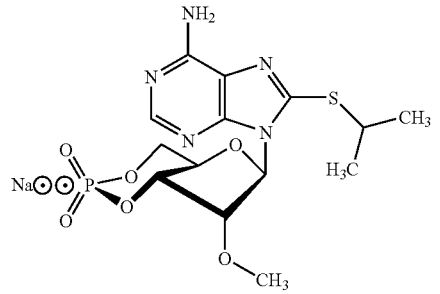 |
| 8-BIT-2'-O—Me-cAMP<br>8-(benzimidazolyl-2-thio)-2'-O-methyladenosine-3',5'-cyclic monophosphate | I-115 | 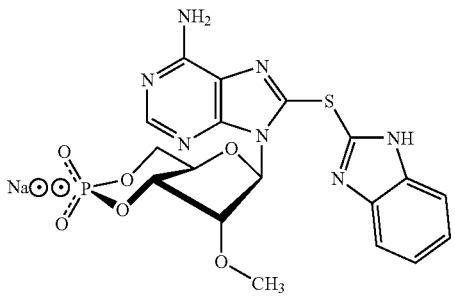 |
| 8-HET-2'-O—Me-cAMP<br>8-(2-hydroxy-ethylthio)-2'-O-methyladenosine-3',5'-cyclic monophosphate | I-116 | 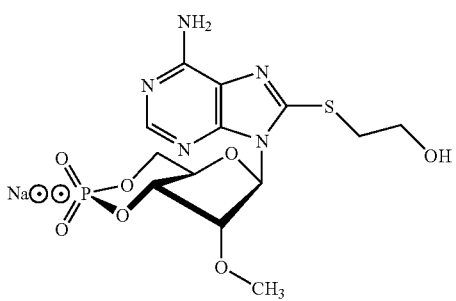 |

TABLE 1-continued

Structures of novel compounds according to the invention.

| Compound | Name | Chemical structure |
|---|---|---|
| 8-ET-2'-O—Me-cAMP<br>8-ethylthio-2'-O-methyladenosine-3',5'-cyclic monophosphate | I-117 | |
| 8-AET-2'-O—Me-cAMP<br>8-(2-aminoethylthio)-2'-O-methyladenosine-3',5'-cyclic monophosphate | I-118 | |
| 8-PyT-2'-O—Me-cAMP<br>8-(pyridinyl-2-thio)-2'-O-methyladenosine-3',5'-cyclic monophosphate | I-119 | |
| 8-BTT-2'-O—Me-cAMP<br>8-(benzothiazolyl-2-thio)-2'-O-methyladenosine-3',5'-cyclic monophosphate | I-120 | |
| 8-pMPT-2'-O—Me-cAMP<br>8-(4-methylphenylthio)-2'-O-methyladenosine-3',5'-cyclic monophosphate | I-121 | |

TABLE 1-continued

Structures of novel compounds according to the invention.

| Compound | Name | Chemical structure |
|---|---|---|
| 8-mMeOPT-2'-O—Me-cAMP<br>8-(3-methoxy-phenylthio)-2'-O-methyladenosine-3',5'-cyclic monophosphate | I-122 | 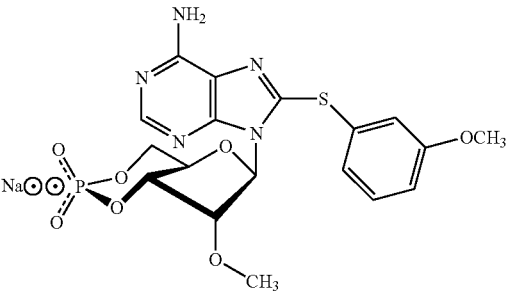 |
| 8-pIPPT-2'-O—Me-cAMP<br>8-(4-isopropyl-phenylthio)-2'-O-methyladenosine-3',5'-cyclic monophosphate | I-123 | 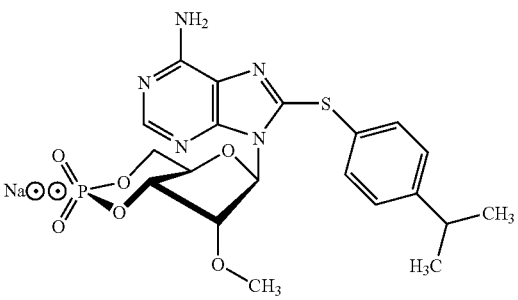 |
| 8-TFPT-2'-O—Me-cAMP<br>8-(2,3,5,6-tetrafluoro-phenylthio)-2'-O-methyladenosine-3',5'-cyclic monophosphate | I-124 | 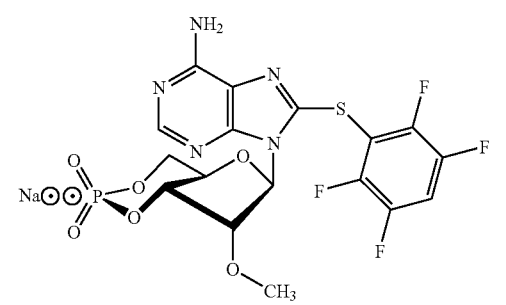 |
| 8-pHPT-2'-O—Me-cAMP<br>8-(4-hydroxy-phenylthio)-2'-O-methyladenosine-3',5'-cyclic monophosphate | I-125 | 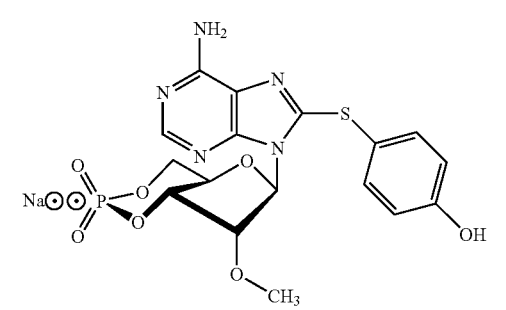 |
| 8-DCPT-2'-O—Me-cAMP<br>8-(2,4-dichloro-phenylthio)-2'-O-methyladenosine-3',5'-cyclic monophosphate | I-126 | 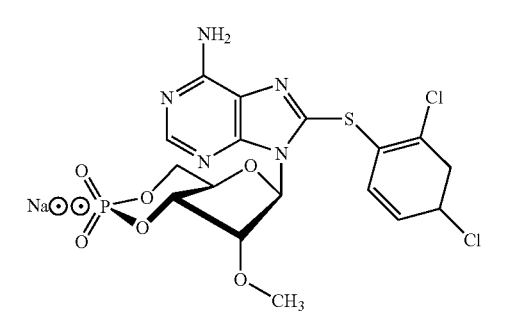 |

TABLE 1-continued

Structures of novel compounds according to the invention.

| Compound | Name | Chemical structure |
|---|---|---|
| 8-pCPT-2'-DMC-cAMP 8-(4-chloro-phenylthio)-2'-(N,N-di-methyl)-carbamoyl-adenosine-3',5'-cyclic monophosphate | I-127 | 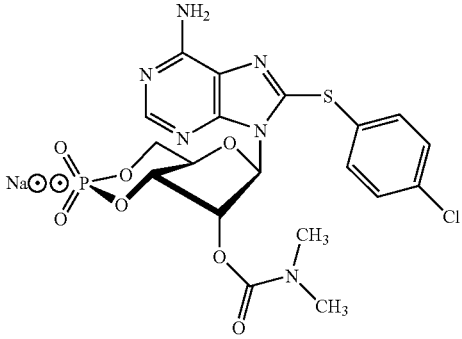 |
| 8-MeO-2'-O—Me-cAMP 8-methoxy-2'-O-methyl-adenosine-3',5'-cyclic monophosphate | I-131 | 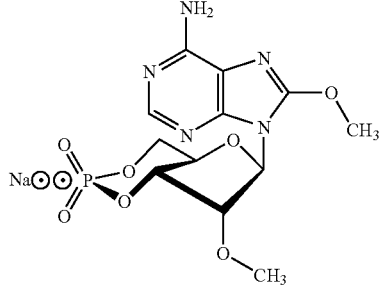 |
| 8-BnO-2'-O—Me-cAMP 8-benzyloxy-2'-O-methyl-adenosine-3',5'-cyclic monophosphate | I-132 | 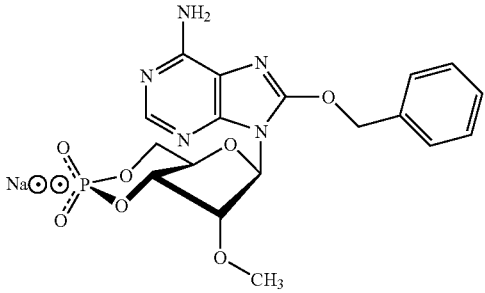 |
| Rp-8-Br-2'-O—Me-cAMPS 8-bromo-2'-O-methyl-adenosine-3',5'-cyclic monophosphorothioate, Rp-isomer | I-129 | 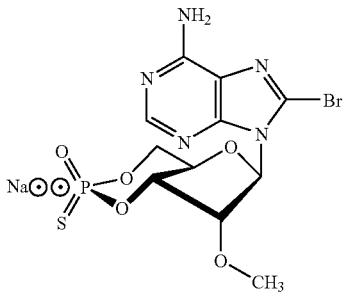 |
| Rp-8-pCPT-2'-O—Me-cAMPS 8-(4-chloro-phenylthio)-2'-O-methyl-adenosine-3',5'-cyclic monophosphorothioate, Rp-isomer | I-130 | 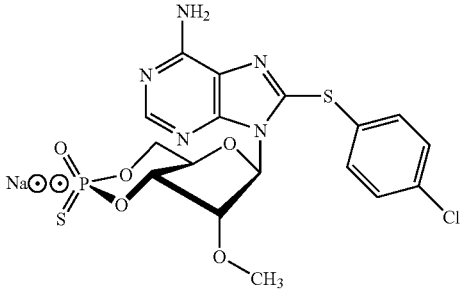 |

TABLE 1-continued

Structures of novel compounds according to the invention.

| Compound | Name | Chemical structure |
|---|---|---|
| Sp-8-Br-2'-O—Me-cAMPS<br>8-bromo-2'-O-methyladenosine-3',5'-cyclic monophosphorothioate, Sp-isomer | I-133 | |
| Sp-8-pCPT-2'-O—Me-cAMPS<br>8-(4-chlorophenylthio)-2'-O-methyladenosine-3',5'-cyclic monophosphorothioate, Sp-isomer | I-134 | |
| Rp-8-Br-2'-dcAMPS<br>8-bromo-2'-deoxyadenosine-3',5'-cyclic monophosphorothioate, Rp-isomer | I-135 | |
| Sp-8-Br-2'-dcAMPS<br>8-bromo-2'-deoxyadenosine-3',5'-cyclic monophosphorothioate, Sp-isomer | I-136 | |
| Rp-8-pCPT-2'-dcAMPS<br>8-(4-chlorophenylthio)-2'-deoxyadenosine-3',5'-cyclic monophosphorothioate, Rp-isomer | I-137 | |
| Sp-8-pCPT-2'-dcAMPS<br>8-(4-chlorophenylthio)-2'-deoxyadenosine-3',5'-cyclic monophosphorothioate, Sp-isomer | I-138 | |

TABLE 1-continued

Structures of novel compounds according to the invention.

| Compound | Name | Chemical structure |
|---|---|---|
| 8-pCPT-cIMP 8-(4-Chloro-phenylthio)-inosine-3',5'-cyclic monophosphate | I-139 | 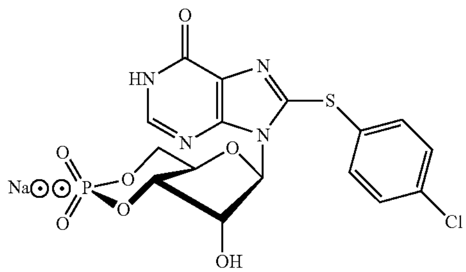 |
| 8-cHA-2'-dcAMP 8-cyclohexylamino-2'-deoxy-adenosine-3',5'-cyclic monophosphate | I-140 | 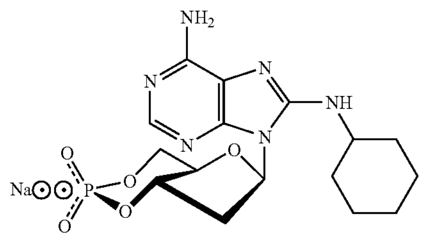 |
| 8-Cl-2'-O—Me-cAMP 8-chloro-2'-O-methyladenosine-3',5'-cyclic monophosphate | I-141 | |

TABLE 2

Effect of the compounds of the invention on PKA and Epac activation in vitro.

| Relative affinity | cAMP = 1 PKAI | PKAII | Epac | Relative activity of Epac* |
|---|---|---|---|---|
| I-001 | 0.00013 | 0.000088 | 0.0025 | + |
| I-002 | 0.01 | 0.00001 | 0.12 | + |
| I-003 | 0.001 | 0.001 | 0.2 | + |
| I-004 | 0.03 | 0.26 | 0.5 | ND |
| I-005 | 0.005 | 0.005 | 0.12 | ND |
| I-006 | 0.0015 | 0.003 | 0.9 | ++ |
| I-007 | 0.009 | 0.003 | 4.6 | +++ |
| I-008 | 0.0043 | | 0.05 | + |
| I-009 | 0.001 | | 0.03 | + |
| I-010 | 0.0008 | | 0.03 | + |
| I-011 | 0.0009 | | 0.017 | ± |
| I-100 | 0.0014 | 0.0001 | <0.5 | ± |
| I-101 | 0.012 | 0.0006 | 1.3 | + |
| I-102 | 0.02 | 0.0004 | 4.5 | +++ |
| I-103 | 0.03 | 0.0005 | 1.8 | ± |
| I-104 | 0.03 | 0.001 | 2.3 | ++ |
| I-105 | 0.02 | 0.0005 | 3.6 | ++ |
| I-106 | 0.02 | 0.0002 | 1.2 | ++ |
| I-107 | 0.004 | 0.0001 | 1.3 | + |
| I-108 | 0.04 | 0.0007 | 1.3 | + |
| I-109 | 0.03 | 0.0008 | 1.2 | ++ |
| I-111 | | | 0.08 | ± |
| I-112 | 0.025 | 0.0006 | 6.5 | +++ |

TABLE 2-continued

Effect of the compounds of the invention on PKA and Epac activation in vitro.

| Relative affinity | cAMP = 1 PKAI | PKAII | Epac | Relative activity of Epac* |
|---|---|---|---|---|
| I-113 | 0.028 | 0.0004 | 0.7 | + |
| I-115 | | | 0.09 | + |
| I-116 | | | 1.2 | + |
| I-117 | | | 1.8 | + |
| I-118 | | | 0.34 | ± |
| I-119 | | | 0.8 | ++ |
| I-120 | | | 0.17 | + |
| I-121 | | | 5.1 | +++ |
| I-122 | | | 2 | + |
| I-123 | | | 4.8 | ++ |
| I-124 | | | 4.7 | ++ |
| I-125 | | | 6.4 | +++ |
| I-126 | | | 3.1 | ++ |
| I-127 | | | <0.002 | − |
| I-129 (Rp-006) | | | 0.05 | ± |
| I-130 (Rp-007) | | | 0.06 | ± |
| I-131 | | | 0.36 | + |
| I-132 | | | 0.18 | + |
| I-133 | | | | + |
| I-134 | | | | + |
| I-135 | | | | + |

TABLE 2-continued

Effect of the compounds of the invention on PKA
and Epac activation in vitro.

| Relative affinity | CAMP = 1 PKAI | PKAII | Epac | Relative activity of Epac* |
|---|---|---|---|---|
| I-136 | | | | + |
| I-137 | | | | + |
| I-138 | | | | + |
| I-139 | | | | + |
| I-140 | | | | + |
| I-141 | 0.012 | 0.0002 | 0.92 | ND |

*relative activity of Epac in vitro in the exchange reaction towards Rap
+++ activity comparible to I-007
++ activity between I-007 and cAMP
+ activity comparible to cAMP
± activity less than cAMP Experimental Procedures Reagents Antibodies against phosphorylated CREB (directed against phosphorylated Ser133) were obtained from Cell Signalling (Beverly, Mass., USA), and antibodies against K-Rev/Rap1 and polyclonal anti-HA were obtained from Santa Cruz Biotechnology (Santa Cruz, Calif., USA). The following inhibitors and stimuli were used at concentrations indicated, unless stated otherwise: RGD peptide (100 μM) and H-89 (10 μM) was obtained from Biomol Research Laboratories Inc. (Plymouth Meeting, Pa., USA). 8-Br-cAMP (1 mM) was obtained from BIOLOG Life Science Institute (Bremen, Germany). TPA (12-O-tetradecanoylphorbol-13-acetate) was obtained from Sigma (Steinheim, Germany) and was used at a concentration of 100 ng/ml.

Cells, Plasmids, Transfections

NIH3T3-A14 cells, stably expressing Epac1, were grown in DMEM with 10% fetal calf serum and 2 μg/ml puromycin. NIH-OVCAR3 (Ovcar3) cells were maintained in RPMI with 10% fetal calf serum. Transient transfection of Ovcar3 cells was performed using the FuGENE 6 transfection reagent (Roche Diagnostics, Mannheim, Germany) according to the manufacturer's procedures, using 6 μg total DNA including a CMV-luciferase plasmid (0.2 μg).

In Vitro Activation of cAMP-Dependent Protein Kinase

Cyclic AMP dependent protein kinase I and II were reconstituted from isolated subunits and assayed for kinase activity using 70 mM kemptide as substrate, as described previously (15).

In Vitro Measurements of Epac Activity

In vitro GEF assays were performed as described (3,16). More specifically, 600 nM Rap1b, loaded with the fluorescent nucleotide mantGDP, was incubated-in the presence of 100-fold excess GTP and in the absence or presence of 150 nM Epac1-ΔDEP1. Increasing concentrations of cAMP or 8-pCPT-2'-O-Me-cAMP were added and single exponential curves were fit to the data to calculate reaction rates. Buffer conditions were 50 mM Tris pH7.4, 150 mM NaCl, 5% glycerol, 5 mM DTE, 60 μM GTP. Reactions were carried out in 96-well plates and measured in a Cary Eclipse from Varian Inc., using the manufacturers software.

Rap1 Activation Assays

Rap activation assays were performed as described previously (16-18). Briefly, cells were lysed in lysis buffer containing 10% glycerol, 1% Nonidet P-40, 50 mM Tris-Cl pH7.5, 200 mM NaCl, 2mM MgCl2, 1 μM leupeptin, 0.1 μM aprotinin, 5 mM NaF, 1 mM NaVO3. Lysates were clarified by centrifugation and incubated with GST-tagged RalGDS-RBD pre-coupled to glutathione beads to specifically pull down the GTP-bound forms of Rap1. Samples were incubated for 1 hr at 4° C. while tumbling. Beads were washed four times in lysis buffer, and the remaining fluid was removed with an insulin syringe. Proteins were eluted with Laemmli sample buffer and analyzed by sodium dodecyl sulphate (SDS)-polyacrylamide gel electrophoresis and Western blotting using Rap1 antibodies. As a control, Rap1 levels in whole cell lysates were determined.

Adhesion Assay 24-well plates were coated overnight with 2 μg/ml fibronectin (Sigma, St. Louis, Mo., USA) in sodium bicarbonate buffer (Sigma, St. Louis, Mo., USA). Poly-L-lysine was coated for 2 hours at room temperature (0.1% w/v in water), washed twice with water and dried overnight. Plates were washed in TSM buffer (20 mM Tris-HCl pH 8, 150 mM NaCl, 1 mM $CaCl_2$, 2 mM $MgCl_2$) and blocked for 30-45 min at 37° C. with 1% BSA/TSM. Transiently transfected Ovcar3 cells, serum-starved 16 h prior to the adhesion assay, were detached by trypsinization. Cells were centrifuged and resuspended in serum-free RPMI containing 25 mM Hepes, 0.5% BSA and 1 g/L glucose to allow recovery of cell surface markers at 37° C. for 1.5-2 h with gentle rotation in suspension. Cells were centrifuged, counted and resuspended at $3\times10^5$ cells/ml in serum-free RPMI with 0.5% BSA. The experiment was performed in triplicates, and to each well 150 μl of cells was added to 150 μl of medium with or without stimulus. In studies with H-89 (10 μM), cells were either preincubated at 37° C. for 30 min with the inhibitor prior to seeding the wells (short pretreatment) or H-89 was added before trypsinization, during the recovery period and before seeding wells (long pretreatment). Cells were allowed to adhere for 1 hour at 37° C. and non-adherent cells were removed by gently washing plates 3 times with warmed 0.5% BSA/TSM. Adherent cells were lysed in luciferase lysis buffer (15% glycerol, 25 mM Tris-phosphate pH 7.8, 1% Triton X-100, 8 mM $MgCl_2$, 1 mM DTT) at 4° C. for 30 min and units of luciferase activity were quantified with addition of equal volume of luciferase assay buffer (25 mM Tris-phosphate pH 7.8, 8 MM $MgCl_2$, 1 mM DTT, 1 mM ATP pH 7, 1 mM luciferin) using a luminometer (Lumat LB9507; Berthold Technologies, Belgium). Unseeded cells (150 μl) were lysed separately to determine luciferase counts in the total input cells. Specific adhesion (%) was determined (counts in cells bound/counts in total input×100) and plotted either directly or relative to the basal adhesion of HA vector-transfected cells. Error bars represent average deviation (SD) among experiments, and where representative experiments are depicted, error bars represent average SD within each experiment. The expression of transfected constructs was confirmed by immunoblotting of total cell lysates.

REFERENCES

1. Robison, G. A., Butcher, R. W. & Sutherland, E. W. Cyclic AMP. Annu Rev Biochem 37, 149-174 (1968).
2. de Rooij, J. et al. Epac is a Rap1 guanine-nucleotide-exchange factor directly activated by cyclic AMP. Nature 396, 474-477 (1998).
3. de Rooij, J. et al. Mechanism of regulation of the Epac family of cAMP-dependent RapGEFs. J Biol Chem 275, 20829-20836 (2000).
4. Kawasaki, H. et al. A family of cAMP-binding proteins that directly activate Rap1. Science 282, 2275-2279 (1998).
5. Su, Y. et al. Regulatory subunit of protein kinase A: structure of deletion mutant with cAMP binding domains. Science 269, 807-813 (1995).

6. Genieser, H.-G., Butt, E., Bottin, U., Dostmann, W., Jastorff, B. Synthesis of 3',5'-cyclic phosphates from unprotected nucleosides. Synthesis 1, 53-54 (1989).
7. Kataoka, S. et al. Studies on the synthesis of compounds related to adenosine-3',5'-cyclic phosphate. VI. Synthesis and cardiac effects of N6,N6,2'-O-trialkyl-, N6,2'-O-dialkyl-, and 2'-O-alkyladenosine-3',5'-cyclic phosphates. Chem Pharm Bull (Tokyo) 38, 1596-1600 (1990).
8. Miller, J. P., Boswell, K. H., Muneyama, K., Simon, L. N., Robins, R. K. & Shuman, D. A. Synthesis and Biochemical Studies of various 8-Substituted Derivatives of Guanosine 3',5'-Cyclic Phosphate, Inosine 3',5'-Cyclic Phosphate, and Xanthosine 3',5'-Cyclic Phosphate. Biochemistry 12, 5310-5319 (1973).
9. Enserink, J. M. et al. A novel Epac-specific cAMP analogue demonstrates independent regulation of Rap1 and ERK. Nat Cell Biol 4, 901-906 (2002).
10. Buczek-Thomas, J. A. et al. Integrin-mediated adhesion and signalling in ovarian cancer cells. Cell Signal 10, 55-63 (1998).
11. Rangarajan, S. et al. Cyclic AMP induces integrin-mediated cell adhesion through Epac and Rap1 upon stimulation of the $\beta_2$-adrenergic receptor. J Cell Biol 160, 487-493, 2003.
12. Genieser, H.-G., Dostmann, W., Bottin, U., Butt, E., Jastorff, B. Synthesis of 3',5'-cyclic phosphorothioates by cyclothiophosphorylation of unprotected nucleosides. Tetrahedron Lett 29, 2803-2804 (1988).
13. Furuta, T., Torigai, H., Osawa, T., and Iwamura, M. Direct esterification of phosphates with various halides and its application to synthesis of cAMP alkyl triesters. J Chem Soc, Perkin Trans 1, 24, 3139-3142 (1993).
14. Kopperud, R. et al. Formation of inactive cAMP-saturated holoenzyme of cAMP-dependent protein kinase under physiological conditions. J Biol Chem 277, 13443-13448 (2002).
15. Franke, B., Akkerman, J. W. & Bos, J. L. Rapid Ca2+-mediated activation of Rap1 in human platelets. EMBO J 16, 252-259 (1997).
16. de Rooij, J. & Bos, J. L. Minimal Ras-binding domain of Raf1 can be used as an activation-specific probe for Ras. Oncogene 14, 623-625 (1997).
17. van Triest, M., de Rooij, J. & Bos, J. L. Measurement of GTP-bound Ras-like GTPases by activation-specific probes. Methods Enzymol 333, 343-348 (2001).

The invention claimed is:
1. A compound having the structural formula (I)

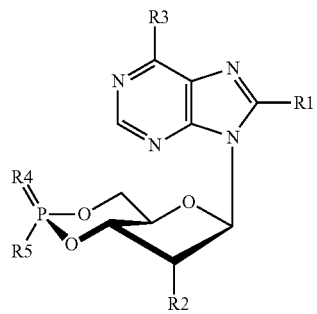

wherein:
R1 can be independently azido, alkyl, aryl, amido-alkyl, amido-aryl, O-alkyl, O-aryl, SH, 2-hydroxyethylthio, 2-aminoethylthio, S-aryl, NH-aryl, N-bisaryl or cycloalkylamino;

R2 can be independently Cl, Br, I, azido, O-alkyl, S-alkyl, NH-alkyl, N-bisalkyl, alkyl-carbamoyl or cycloalkylamino;
R3 can be independently azido, amido-alkyl, amido-aryl, amino, NH-alkyl, NH-aryl, N-bisalkyl, N-bisaryl, NH-alkyl-carbamoyl or cycloalkylamino;
and wherein
R4 is O(H) or S(H); and
R5 is O(H), S(H), amino, H, alkyl, O-alkyl, O-aryl, S-alkyl, S-aryl, NH-alkyl, NH-aryl, N-bisalkyl or N-bisaryl; or
R4 is O(H), S(H), amino, H, alkyl, O-alkyl, O-aryl, S-alkyl, S-aryl, NH-alkyl, NH-aryl, N-bisalky or N-bisaryl; and
R5 is O(H) or S(H);
and pharmaceutically acceptable salts and/or hydrates thereof, with the proviso that the following named compounds are excluded:
2'-deoxyadenosine-3',5'-cyclic amonophosphate;
$N^6$-monobutyryl-2'-deoxyadenosine-3',5'-cyclic monophosphate;
2'-deoxyadenosine-3',5'-cyclic monophosphorothioate;
2'-deoxyadenosine-3',5'-cyclic monophosphoroanilidate;
2'-deoxyadenosine-3',5'-cyclic monophosphate methyl triester;
2'-deoxyadenosine-3',5'-cyclic monophosphate ethyl triester;
2'-O-methyladenosine-3',5'-cyclic monophosphate;
2'-O-ethyladenosine-3',5'-cyclic monophosphate;
2'-O-n-propyladenosine-3',5'-cyclic monophosphate;
2'-O-n-butyladenosine-3',5'-cyclic monophosphate;
2'-O-iso-butyladenosine-3',5'-cyclic monophosphate;
2'-O-methyladenosine-3',5'-cyclic monophosphate methyl triester; and
2'-O-methyladenosine-3',5'-cyclic monophosphate phenyl triester.
2. The compound of claim 1, wherein
R1 is azido, O-alkyl, O-aryl, S-alkyl, S-aryl, NH-alkyl or NH-aryl.
3. The compound of claim 1, wherein
R1 is azido, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 4-methylcumarinyl, naphtyl-2-thio, phenylthio, 4-nitrophenylthio, 2-aminophenylthio, 3-aminophenylthio, 4-aminophenylthio, benzylthio, phenylethylamino, 3-phenyl-propylamino, 2-methoxyphenylthio, 3-methoxyphenylthio, 4-methoxyphenylthio, benzimidazolyl-2-thio, 2-hydroxyethylthio, 2-aminoethylthio,-pyridinylthio, benzothiazolylthio, 2-methylphenylthio, 3-methylphenylthio, 4-methylphenylthio, 2-isopropylphenylthio, 4-isopropylphenylthio, 2,3,5,6-tetrafluorophenylthio, 4-hydroxyphenylthio, 2,4-dichlorophenylthio, methoxy, ethoxy, propioxy, butoxy, benzyloxy, 4-methylbenzyloxy, 4-methoxybenzyloxy, 4-fluorobenzyloxy, 4-chlorobenzyloxy, 4-bromobenzyloxy, phenyloxy, cyclohexylamino, benzylamino, 4-isopropyloxyphenylthio, 4-methylthiophenylthio, 6-aminohexylamino, 2,3-dichlorophenylthio, 2,5-dichlorophenylthio, 2,4-difluorophenylthio, 2,5-dimethoxyphenylthio, 2,5-dimethylthiophenylthio, 2,6-dimethylthiophenylthio or 2,6-dichlorophenylthio.
4. The compound of claim 1, wherein
R1 is azido, 2-chlorophenylthio, 3-chlorophenylthio, 4-chlorophenylthio, 2-bromophenylthio, 3-bromophenylthio, 4-bromophenylthio, 2-fluorophenylthio, 3-fluorophenylthio, 4-fluorophenylthio, 4-methylcumarinyl, naphtyl-2-thio, phenylthio, 4-nitrophenylthio, 2-aminophenylthio, 3-aminophenylthio, 4-aminophenylthio, benzylthio, phenylethylamino, 2-methoxyphenylthio, 3-methoxyphenylthio, 4-methoxyphenylthio, isopropylthio, benzimidazolyl-2-thio, 2-hydroxyethylthio, 2-aminoethylthio, pyridinylthio, benzothiazolylthio, 2-methylphenylthio, 3-methylphenylthio, 4-methylphenylthio, 2-isopropylphenylthio, 4-isopropylphenylthio, 2,3,5,6-tetrafluorophenylthio, 4-hydroxyphenylthio, 2,4-dichlorophenylthio, methoxy, benzyloxy, cyclohexylamino, benzylamino, 4-isopropyloxyphenylthio, 4-methylthiophenylthio, 6-aminohexylamino, 2,3-dichlorophenylthio, 2,5-dichlorophenylthio, 2,4-difluorophenylthio, 2,5-dimethoxyphenylthio, 2,5-dimethylthiophenylthio, 2,6-dimethylthiophenylthio or 2,6-dichlorophenylthio.

5. The compound of claim 1, wherein
R1 is azido, 4-chlorophenylthio, methylamino, methylthio, 4-fluorophenylthio, 4-methylcumarinyl, naphtyl-2-thio, phenylthio, 4-nitrophenylthio, 2-aminophenylthio, benzylthio, n-hexylthio, phenylethylamino, 4-methoxyphenylthio, isopropylthio, benzimidazolyl-2-thio, 2-hydroxyethylthio, ethylthio, 2-aminoethylthio, pyridinylthio, benzothiazolylthio, 4-methylphenylthio, 3-methoxyphenylthio, 4-isopropylphenylthio, 2,3,5,6-tetrafluorophenylthio, 4-hydroxyphenylthio, 2,4-dichlorophenylthio, methoxy, benzyloxy, cyclohexylamino, benzylamino, 4-isopropyloxyphenylthio, 4-methylthiophenylthio or 6-aminohexylamino.

6. The compound of claim 1, wherein
R1 is S-aryl.

7. The compound of claim 1, wherein
R1 is 4-chlorophenylthio, 4-fluorophenylthio, naphtyl-2-thio, phenylthio, 4-nitrophenylthio, 4-methoxyphenylthio, pyridinyl-2-thio, 4-methylphenylthio, 4-isopropylphenylthio, 2,3,5,6-tetrafluoro-phenylthio, 4-hydroxyphenylthio, or 2,4-dichloro-phenylthio.

8. The compound of claim 6, wherein
R1 is 4-chlorophenylthio, 4-fluorophenylthio, 4-methoxyphenylthio, 4-methylphenylthio or 4-hydroxyphenylthio.

9. The compound of claim 1, wherein
R2 is Cl, Br, I, azido, O-alkyl or S-alkyl.

10. The compound of claim 1, wherein
R2 is Cl, Br, I, O-alkyl, S-methyl or S-ethyl.

11. The compound of claim 1, wherein
R2 is Cl, Br, O-methyl, O-ethyl, O-propyl, O-butyl, O-isobutyl or S-methyl.

12. The compound of claim 1, wherein
R2 is O-methyl, O-ethyl, O-propyl, O-butyl or O-isobutyl.

13. The compound of claim 1, wherein
R2 is O-methyl.

14. The compound of claim 1, wherein
R3 is amino, NH-alkyl, N-bisalkyl, NH-aryl, NH-alkylcarbamoyl, N-bisalkyl-carbamoyl, amido-alkyl or amido-aryl.

15. The compound of claim 1, wherein
R3 is amino, NH-phenyl, NH-tert-butyl, NH-tert-butylcarbamoyl, NH-phenylcarbamoyl, NH-acetyl, NH-propionyl, NH-butyryl, NH-benzoyl, NH-benzyl, NH-phenylethyl, NH-phenylpropyl, N-bismethyl or N-bisethyl.

16. The compound of claim 1, wherein
R3 is amino, NH-phenyl, NH-tert-butyl, NH-tert-butylcarbamoyl, NH-phenylcarbamoyl; NH-butyryl, NH-benzoyl, NH-benzyl, N-bismethyl or N-bisethyl.

17. The compound of claim 1, wherein
R3 is amino, NH-phenyl, NH-tert-butyl, NH-tert-butylcarbamoyl, NH-benzoyl or N-bismethyl.

18. The compound of claim 1, wherein R3 is amino or NH-tert-butyl.

19. The compound of claim 1, wherein R4 and R5 are independently O(H) or S(H).

20. The compound of claim 1, wherein R4 and R5 are O(H).

21. The compound of claim 1, wherein R1 is 4-chlorophenylthio and R2 is O-methyl.

22. A pharmaceutical composition comprising the composition of claim 21 and one or more pharmaceutically acceptable excipients.

23. A compound selected from the group consisting of:
8-(4-chloro-phenylthio)-2'-deoxyadenosine-3',5'-cyclic monophosphate;
8-(4-chloro-phenylthio)- $N^6$-phenyl-2'-deoxyadenosine-3',5'-cyclic monophosphate;
8-(4-chloro-phenylthio)-2'-O-methyladenosine-3',5'-cyclic monophosphate;
8-(4-fluoro-phenylthio)-2'-O-methyladenosine-3',5'-cyclic monophosphate;
8-(4-methyl-cumarinyl-7-thio)-2'-O-methyladenosine-3',5'-cyclic monophosphate;
8-(naphtyl-2-thio)-2'-O-methyladenosine-3',5'-cyclic monophosphate;
8-phenylthio-2'-O-methyladenosine-3',5'-cyclic monophosphate;
8-(4-nitro-phenylthio)-2'-O-methyladenosine-3',5'-cyclic monophosphate;
8-(2-amino-phenylthio)-2'-O-methyladenosine-3',5'-cyclic monophosphate;
8-benzylthio-2'-O-methyladenosine-3',5'-cyclic monophosphate;
8-phenylethylamino-2'-O-methyladenosine-3',5'-cyclic monophosphate;
8-(4-methoxy-phenylthio)-2'-O-methyladenosine-3',5'-cyclic monophosphate;
8-(benzimidazolyl-2-thio)-2'-O-methyladenosine-3',5'-cyclic monophosphate;
8-(2-hydroxy-ethylthio)-2'-O-methyladenosine-3',5'-cyclic monophosphate;
8-(2-amino-ethylthio)-2'-O-methyladenosine-3',5'-cyclic monophosphate;
8-(pyridinyl-2-thio)-2'-O-methyladenosine-3',5'-cyclic monophosphate;
8-(benzothiazolyl-2-thio)-2'-O-methyladenosine-3',5'-cyclic monophosphate;
8-(4-methyl-phenylthio)-2'-O-methyladenosine-3',5'-cyclic monophosphate;
8-(3-methoxy-phenylthio)-2'-O-methyladenosine-3',5'-cyclic monophosphate;
8-(4-isopropyl-phenylthio)-2'-O-methyladenosine-3',5'-cyclic monophosphate;
8-(2,3,5,6-tetrafluoro-phenylthio)-2'-O-methyladenosine-3',5'-cyclic monophosphate;
8-(4-hydroxy-phenylthio)-2'-O-methyladenosine-3',5'-cyclic monophosphate;
8-(2,4-dichloro-phenylthio)-2'-O-methyladenosine-3',5'-cyclic monophosphate;
8-(4-chloro-phenylthio)-2'-(N,N-dimethyl)-carbamoyladenosine-3',5'-cyclic monophosphate;
8-benzyloxy-2'-O-methyladenosine-3',5'-cyclic monophosphate;
8-bromo-2'-O-methyladenosine-3',5'-cyclic monophosphorothioate, Sp-isomer;
8-bromo-2'-O-methyladenosine-3',5'-cyclic monophosphorothioate, Rp-isomer, 8-(4-chloro-phenylthio)-2'-O-methyladenosine-3',5'-cyclic monophosphorothioate, Sp-isomer;
8-(4-chloro-phenylthio)-2'-O-methyladenosine-3',5'-cyclic monophosphorothioate, Rp-isomer;
8-bromo-2'-deoxyadenosine-3',5'-cyclic monophosphorothioate, Rp-isomer;
8-bromo-2'-deoxyadenosine-3',5'-cyclic monophosphorothioate, Sp-isomer;
8-(4-chloro-phenylthio)-2'-deoxyadenosine-3',5'-cyclic monophosphorothioate, Rp-isomer;
8-(4-chloro-phenylthio)-2'-deoxyadenosine-3',5'-cyclic monophosphorothioate, Sp-isomer;
8-cyclohexylamino-2'-deoxyadenosine-3',5'-cyclic monophosphate; and
$N^6$-tert-butyl-8-(4-chloro-phenylthio)-2'-deoxyadenosine-3',5'-cyclic monophosphate.

24. The compound of claim 23 wherein said compound is 8-(4-chloro-phenylthio)-2-Omethyladenosine-3',5'-cyclic monophosphate.

25. The compound of claim 23 wherein said compound is 8-(naphtyl-2-thio)-2'-O-methyladenosine-3',5'-cyclic monophosphate.

26. The compound of claim 23 wherein said compound is 8-phenylthio-2'-O-methyladenosine-3',5'-cyclic monophosphate.

27. The compound of claim 23 wherein said compound is 8-(4-nitro-phenylthio)-2'-O-methyladenosine-3',5'-cyclic monophosphate.

28. A compound wherein said compound is 8-n-hexylthio-2'-O-methyladenosine-3',5'-cyclic monophosphate.

29. The compound of claim 23 wherein said compound is 8-(4-methoxy-phenylthio)-2'-O-methyladenosine-3',5'-cyclic monophosphate.

30. The compound of claim 23 wherein said compound is 8-(benzothiazolyl-2-thio)-2'-O-methyladenosine-3',5'-cyclic monophosphate.

31. The compound of claim 23 wherein said compound is 8-(4-methyl-phenylthio)-2'-O-methyladenosine-3',5'-cyclic monophosphate.

32. The compound of claim 23 wherein said compound is 8-(4-isopropyl-phenylthio)-2'-O-methyladenosine-3',5'-cyclic monophosphate.

33. The compound of claim 23 wherein said compound is 8-(2,3,5,6-tetrafluoro-phenylthio)-2'-O-methyladenosine-3',5'-cyclic monophosphate.

34. The compound of claim 23 wherein said compound is 8-(4-hydroxy-phenylthio)-2-O-methyladenosine-3',5'-cyclic monophosphate.

35. The compound of claim 23 wherein said compound is 8-(2,4-dichloro-phenylthio)-2'-O-methyladenosine-3',5'-cyclic monophosphate.

36. A pharmaceutical composition comprising the compound of claim 1 or 23, and one or more pharmaceutically acceptable excipients.

* * * * *